United States Patent
Shigemitsu et al.

(10) Patent No.: US 11,385,244 B2
(45) Date of Patent: Jul. 12, 2022

(54) METHOD OF MEASURING STABLE A1C

(71) Applicant: ARKRAY, Inc., Kyoto (JP)

(72) Inventors: Takanari Shigemitsu, Kyoto (JP); Jin Yoshida, Kyoto (JP)

(73) Assignee: ARKRAY, INC., Kyoto (JP)

( * ) Notice: Subject to any disclaimer, the term of this patent is extended or adjusted under 35 U.S.C. 154(b) by 17 days.

(21) Appl. No.: 16/905,106

(22) Filed: Jun. 18, 2020

(65) Prior Publication Data

US 2020/0400690 A1    Dec. 24, 2020

(30) Foreign Application Priority Data

Jun. 21, 2019  (JP) .............................. JP2019-115639
Jun. 21, 2019  (JP) .............................. JP2019-115640
Apr. 30, 2020  (JP) .............................. JP2020-080798

(51) Int. Cl.
*G01N 33/72*    (2006.01)
*G01N 27/447*   (2006.01)

(52) U.S. Cl.
CPC ..... *G01N 33/721* (2013.01); *G01N 27/44769* (2013.01); *G01N 33/723* (2013.01)

(58) Field of Classification Search
CPC ........... G01N 27/447; G01N 27/44721; G01N 27/44769; G01N 33/49; G01N 33/721; G01N 33/723
USPC ..... 436/63, 66, 67, 149, 150, 161, 164, 172; 422/70, 82.01, 82.05, 82.08, 82.09, 503, 422/507
See application file for complete search history.

(56) References Cited

U.S. PATENT DOCUMENTS

| | | | |
|---|---|---|---|
| 8,257,567 B2* | 9/2012 | Oishi | G01N 27/44747 204/451 |
| 9,017,536 B2* | 4/2015 | Oishi | C07K 1/26 204/451 |
| 2009/0200166 A1* | 8/2009 | Nakayama | C07K 1/16 204/451 |

(Continued)

FOREIGN PATENT DOCUMENTS

| | | |
|---|---|---|
| JP | 2004-069640 A | 3/2004 |
| JP | 2008-139866 A | 6/2008 |

(Continued)

OTHER PUBLICATIONS

Doelman et al. Clinical Chemistry, vol. 43:4, pp. 644-648, 1997.*
Extended European Search Report issued in corresponding European Patent Application No. 20181168.4 dated Nov. 12, 2020.

*Primary Examiner* — Maureen Wallenhorst
(74) *Attorney, Agent, or Firm* — Morgan, Lewis & Bockius LLP

(57) ABSTRACT

A method of measuring stable A1c in a blood sample based on a time distribution of an optical measured value of hemoglobin at a flow path which separates hemoglobin in the blood sample on a basis of amounts of the charges of hemoglobin is provided. The method may include a step of obtaining a correction factor, based on a peak area (A) of a fraction including HbA0 and either a peak area (G) of a first fraction including chemically-modified HbA0, or a peak area (D) of a second fraction including a component having a smaller amount of positive charge than HbA0 adjacent to a fraction identified as HbA0, in the time distribution; and a step of correcting, based on the correction factor a peak area of a fraction including stable A1c in the time distribution.

13 Claims, 33 Drawing Sheets

(56) References Cited

U.S. PATENT DOCUMENTS

2011/0000788 A1* 1/2011 Deschamps ...... G01N 27/44791
                                                    204/451
2019/0120803 A1* 4/2019 Hasegawa .............. G01N 33/49

FOREIGN PATENT DOCUMENTS

JP    2008-170350 A    7/2008
JP    2009-186445 A    8/2009

* cited by examiner

METHOD OF MEASURING STABLE A1C

CROSS-REFERENCE TO RELATED APPLICATION

This application claims priority under 35 USC 119 from Japanese Patent Applications Nos. 2019-115639 and 2019-115640 both filed on Jun. 21, 2019, and 2020-080798 filed on Apr. 30, 2020, the disclosures of which are incorporated by reference herein.

BACKGROUND

Technical Field

The present invention relates to a method of measuring stable hemoglobin A1c in a fraction of bloodstream hemoglobin.

Related Art

HbA1c is hemoglobin in which glucose binds to the N-terminal valine residue of a β chain of the hemoglobin molecule. In further detail, stable hemoglobin A1c (stable HbA1c, hereinafter referred to as "stable A1c" or "S-A1c") that is an irreversible reaction product is generated through labile A1c (labile HbA1c, hereinafter referred to as "labile A1c" or "L-A1c") that is generated reversibly. Stable A1c clinically reflects an average blood sugar level over previous one to two months, and is crucial as an index for diabetes management.

HPLC, immunoassay, capillary electrophoresis, and the like are conventionally used as methods of measuring HbA1c. A method of analyzing hemoglobin by capillary electrophoresis is disclosed in Japanese Patent Application Reissue No. 2008-139866.

In a case of measuring stable A1c by HPLC or capillary electrophoresis, the stable A1c is separated from bloodstream hemoglobin, and a proportion thereof with respect to a total hemoglobin is derived from a size of a peak obtained by the separation.

At this time, in a patient with renal failure, for example, hemoglobin is subjected to chemical modification by carbamylation in which cyanate generated from urea binds with hemoglobin. Further, for example, the hemoglobin can also be subjected to chemical modification by aldehydation in which acetaldehyde in blood binds with hemoglobin.

Due to elution of a hemoglobin fraction chemically modified in this way at the same time as the fraction expressing stable A1c, the apparent stable A1c is measured as a value higher than it actually is (Japanese Patent Application Laid-Open (JP-A) No. 2004-69640), or there are cases in which the proportion of the stable A1c fluctuates greatly (JP-A No. 2008-170350).

Accordingly, in order to accurately measure stable A1c, the hemoglobin chemically modified in this way must be sufficiently separated. Thus, an attempt has been made, in capillary electrophoresis, to separate stable A1c from chemically-modified hemoglobin by changing a coating of an inner surface of a capillary or migration conditions (JP-A No. 2008-170350 and JP-A No. 2009-186445).

As described above, studies have been carried out on avoiding the effects that the existence of chemically-modified hemoglobin has on the measurement of stable A1c by separating carbamylated hemoglobin generated by cyanate generated from the urea of a patient with renal failure or aldehydated hemoglobin generated by acetaldehyde within the blood, from stable A1c. However, more accurate measurement of a proportion of stable A1c in blood containing cyanate or acetaldehyde is desired.

Stable A1c itself also is hemoglobin, and is subjected to chemical modification such as carbamylation or aldehydation. Therefore, in order to derive a proportion of stable A1c that reflects an average blood sugar level over previous one to two months, both the stable A1c that is chemically modified and the stable A1c that is not chemically modified must be derived. However, in conventional separation analysis techniques, a peak area of a fraction containing stable A1c that is not chemically modified is measured, and a proportion of stable A1c reflecting the average blood sugar level over previous one to two months is derived from the results thereof. A peak area of a fraction including chemically-modified stable A1c is not considered in deriving the proportion of stable A1c. Therefore, as has been attempted conventionally, even if an attempt is made in separation analysis to separate and elute the fraction of hemoglobin that is chemically modified and the fraction of stable A1c that is not chemically modified, a proportion of stable A1c, which reflects the average blood sugar level over previous one to two months of a patient with renal failure or a patient having a high aldehyde concentration in the blood, cannot be measured accurately, and diabetes management cannot be carried out appropriately.

SUMMARY

A method of measuring stable A1c of the present disclosure is a method of measuring stable A1c in a blood sample based on a time distribution of an optical measured value of hemoglobin at a flow path which separates hemoglobin in the blood sample on a basis of amounts of the charges of hemoglobin, the method comprising: a step of obtaining a correction factor, based on a peak area (A) of a fraction including HbA0 and either a peak area (G) of a first fraction including chemically-modified HbA0, or a peak area (D) of a second fraction including a component having a smaller amount of positive charge than HbA0 adjacent to a fraction identified as HbA0, in the time distribution; and a step of correcting, based on the correction factor a peak area of a fraction including stable A1c in the time distribution.

Note that it is thought that, in a sample in which HbA0 is chemically modified, the stable A1c is carbamylated or aldehydated. Therefore, it was discovered that, in a sample in which it is judged that the HbA0 is chemically modified, it is necessary to derive the proportions of both the stable A1c that is not chemically modified and the stable A1c that is chemically modified. On the other hand, for example, a fraction including chemically-modified HbA0 in the electropherogram obtained by separating and analyzing the sample by capillary electrophoresis, also includes labile A1c in addition to the chemically-modified HbA0. Therefore, the peak area of the fraction including chemically-modified HbA0 fluctuates in accordance with an amount of the labile A1c contained in the sample, and whether or not the sample is a sample in which HbA0 is chemically modified cannot be distinguished from a magnitude of the peak area of the fraction including chemically-modified HbA0. Therefore, it was discovered that, at the time of deriving the proportion of stable A1c, it is necessary to appropriately judge whether or not the sample is a sample for which there is a strong need to consider the proportion of chemically-modified stable A1c.

Thus, it is desirable that the above-described method of measuring stable A1c of the present disclosure also comprises: a step of distinguishing whether or not a first proportion (ratio) is greater than or equal to a first threshold value, the first proportion representing a proportion of the peak area (D) of the second fraction, with respect to either the peak area (A) of the fraction including HbA0, or the entire peak area of the fractions including hemoglobin in the time distribution; and a step of, in a case in which the first proportion is greater than or equal to the first threshold value, correcting the peak area of the fraction including stable A1c using the correction rate.

In embodiments of the present invention, the amount of stable A1c can be measured more accurately by considering the amount of chemically-modified stable A1c.

BRIEF DESCRIPTION OF THE DRAWINGS

Exemplary embodiments will be described in detail based on the following figures, wherein.

DETAILED DESCRIPTION

Figure 1:
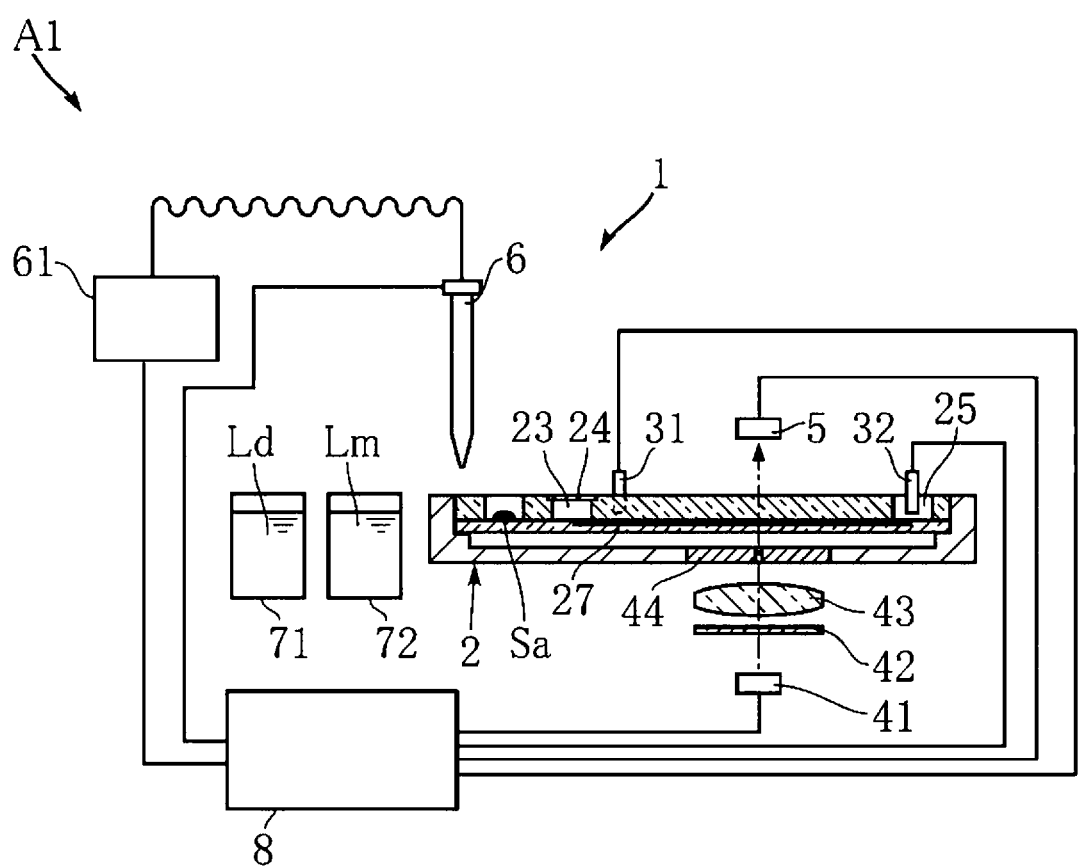
FIG. 1 is a system schematic drawing showing an example of an analyzing system.

The method of measuring stable A1c of the present disclosure is a method of measuring stable A1c in a blood sample based on a time distribution of an optical measured value of hemoglobin at a flow path which separates hemoglobin in the blood sample on the basis of amounts of the charges of hemoglobin, the method comprising: a step of obtaining a correction factor, based on a peak area (A) of a fraction including HbA0 and either a peak area (G) of a first fraction including chemically-modified HbA0, or a peak area (D) of a second fraction including a component having a smaller amount of positive charge than HbA0 adjacent to a fraction identified as HbA0, in the time distribution; and a step of correcting, based on the correction factor a peak area of a fraction including stable A1c in the time distribution.

The exact method of the aforementioned separation analysis is not particularly limited provided that it is a method that can separate the types of hemoglobin on the basis of amounts of the molecular surface charges of hemoglobin. HPLC (High Performance Liquid Chromatography) and capillary electrophoresis are examples thereof. Of these examples, capillary electrophoresis is suitable from the standpoint of analyzing, in a short time, more samples owing to a more simple measuring system.

The time distribution of hemoglobin expresses a signal strength and a time, at which the hemoglobin is separated within a flow path and each separated hemoglobin is detected at a measuring region that is a specific location on the flow path, on a graph in which time is plotted on the horizontal axis and signal strength is plotted on the vertical axis. The time on the horizontal axis expresses a time needed for the hemoglobin to move a predetermined distance. The time on the horizontal axis can also be referred to as a time period which is from the point in time that separation is started to the point in time when a sample component is detected at the measuring region at a specific location on the flow path. The time distribution of hemoglobin encompasses, for example, a chromatogram obtained from chromatography, or an electropherogram obtained from capillary electrophoresis.

For example, in the case of capillary electrophoresis or HPLC based on the principles of ion exchange, a moving speed fluctuates in accordance with an amount of charges of a hemoglobin molecular surface. Therefore, the elapsed time period from the start of separation until the hemoglobin molecule moves within the capillary channel or within the column and passes a specific location, i.e., the time period required for the hemoglobin molecule to move a predetermined distance, can be considered to be the amount of the molecular surface charge of the hemoglobin molecule. Further, the strength of the signal (e.g., the absorbance), which corresponds to the time elapsed from the start of migration, is expressed as a curve having several peaks and bottoms (troughs), i.e., as a electropherogram or a chromatogram. The hemoglobin is separated into several fractions on the basis of a shape of the electropherogram or the chromatogram. For example, a fraction whose center is a specific peak is identified as a specific component of the hemoglobin.

It suffices for a value that expresses the magnitude of the molecular surface charges to be plotted on the horizontal axis of the time distribution of the hemoglobin. Therefore, other than the time period required for moving a predetermined distance as described above, the value may be the moving speed of each hemoglobin molecule, or may be the distance moved in a specific time period. It suffices for the amount of hemoglobin to be plotted on the vertical axis of the time distribution of the hemoglobin. For example, the contained amount of hemoglobin itself, or the concentration of hemoglobin, may be used. Further, the value may be a signal strength outputted from a detector at the measuring region, or may be an optical measured value such as absorbance, the fluorescence or the emitted light intensity. Further, the amount of change of the change in absorbance per unit time may be used. In consideration of an absorption spectrum of hemoglobin, it is desirable to measure an absorbance of a wavelength of 415 nm or a vicinity thereof, and for the absorbance to be on the vertical axis. A peak area and height of the peak of a fraction obtained from the shape of the time distribution of the hemoglobin are an optical measured value and expresses an amount of these separated hemoglobin molecules.

When hemoglobin within blood is separated and analyzed by a separation analysis method based on principles of cation exchange as in the case of capillary electrophoresis in the present Examples, the respective hemoglobins are detected in order from hemoglobin having a smaller positive charge amount to hemoglobin having a larger positive charge amount. Specifically, a fraction including HbF is detected, and, thereafter, a fraction including chemically-modified HbA0 and labile A1c is detected. After that, a fraction including stable A1c, a fraction adjacent to the fraction including HbA0, and a fraction including HbA0 are detected in this order. Here, the detected fraction including stable A1c is a fraction derived from stable A1c that remains without having been chemically modified. A remaining rate (a correction factor), which is a proportion of the HbA0 that remains without having been chemically modified, is derived from the peak area of the fraction including chemically-modified HbA0, or the peak area of the fraction having a smaller amount of positive charge adjacent to the fraction identified as HbA0, which have been obtained by the separation analysis.

The chemical modification in the present disclosure is, for example, at least one of carbamylation or aldehydation.

The remaining rate (a correction factor) may be a proportion of the peak area of the fraction including HbA0, with respect to the total value of the peak area of the fraction including HbA0 and the peak area of the fraction including the chemically-modified HbA0. Further, the remaining rate may be derived by using a modification rate which is a proportion of the peak area of the fraction including chemically-modified HbA0, with respect to the total value of the peak area of the fraction including HbA0 and the peak area of the fraction including chemically-modified HbA0. For example, the remaining rate may be derived by subtracting the modification rate from 1. This remaining rate can also be referred to as a proportion of the amount of HbA0 that is not chemically modified, with respect to the total amount of the HbA0 that is not chemically modified and the HbA0 that is chemically modified. On the other hand, the modification rate can also be referred to as a proportion of the amount of chemically-modified HbA0 with respect to the total amount of the HbA0 that is not chemically modified and the HbA0 that is chemically modified.

The derivation of the modification rate is described hereinafter. The HbA0 amount occupies a majority of the total amount, which is contained in blood, of the HbA0 amount that is not chemically modified (note that, when simply "HbA0" is used in the present disclosure, it means the HbA0 that is not chemically modified) and the HbA0 amount that is chemically modified. Therefore, the peak area of the fraction including HbA0 occupies a majority of the total value of the peak area of the fraction including HbA0 and the peak area of the fraction including chemically-modified HbA0, which are obtained from the time distribution of the hemoglobin. Accordingly, the modification rate may be derived by considering the peak area of the fraction including HbA0 to be the total value of the peak area of the fraction including HbA0 and the peak area of the fraction including chemically-modified HbA0. Further, HbA0 accounts for a majority of the hemoglobin contained in blood. Therefore, the peak area of the fraction including HbA0 occupies a majority of the entire peak area of the fractions including hemoglobin obtained from the time distribution of hemoglobin. Accordingly, the modification rate may be derived by considering the peak area of the fraction including HbA0 to be the entire peak area of the fractions including hemoglobin. Further, for the same reason, the modification rate may be derived by considering the entire peak area of the fractions including hemoglobin to be the total value of the peak area of the fraction including HbA0 and the peak area of the fraction including chemically-modified HbA0.

Note that, in the present disclosure, the peak area of all of the fractions obtained from the shape of the time distribution of the hemoglobin may be used as the entire peak area of the fractions including hemoglobin.

The fraction (the first fraction) including chemically-modified HbA0 is a fraction having a smaller amount of positive charge adjacent to a fraction identified as stable A1c. The fraction can also be referred to as a fraction that exists at a side, at which the positive charge amount is larger, of HbF. In other words, the fraction can also be referred to as a fraction which exists at a side, at which the positive charge amount is smaller, of the fraction identified as stable A1c, and that exists at a side, at which the positive charge amount is larger, of HbF. In other words, the fraction can be referred to as a fraction having a smaller amount of positive charge adjacent to a fraction identified as stable A1c, and that exists at a side, at which the positive charge amount is larger, of HbF. In other words, the fraction including the chemically-modified HbA0 is a fraction whose detection time is earlier than that of a fraction identified as stable A1c, or can also be referred to as the fraction whose detection time is later than that of HbF. In other words, the fraction can also be referred to as the fraction whose detection time is earlier than that of the fraction identified as stable A1c, and whose detection time is later than that of HbF. The fraction including the chemically-modified HbA0 includes carbamylated HbA0 or aldehydated HbA0 as a known component. The peak area of the fraction including chemically-modified HbA0 increases when the hemoglobin is carbamylated or aldehydated.

For the peak area of the fraction including chemically-modified HbA0, the numerical value may be used as is, or a numerical value corrected appropriately may be used. For example, in a case in which a component other than the chemically-modified HbA0 is included in the fraction including the chemically-modified HbA0, a value may be used obtained by deducting the peak area, which is derived from the component other than the chemically-modified HbA0, from the peak area of the fraction including chemically-modified HbA0. In a case in which the peak area derived from the component other than the chemically-modified HbA0 is known, the known peak area may be deducted as a predetermined peak area. Further, samples of plural healthy individuals may be separated and analyzed, and a predetermined peak area as a statistical value of the peak area of a component other than the HbA0 subjected to chemical modification, may be determined in advance before measurement of the stable A1c of the sample. Then, when measuring the sample, the predetermined peak area may be deducted from the peak area of the fraction including the chemically-modified HbA0. For example, the peak area corrected value as the statistical value is an average value or a median value or the like.

Further, the remaining rate and the modification rate may be derived by using the fraction (the second fraction) having a smaller amount of positive charge adjacent to the fraction identified as HbA0. The second fraction is obtained only after hemoglobin is separated by capillary electrophoresis. Although the reason therefor is not certain, the peak area of the fraction having a smaller amount of positive charge adjacent to the fraction identified as HbA0 increases when hemoglobin is carbamylated or aldehydated. Accordingly, for example, the sample of a healthy individual may be artificially carbamylated, and a correlation relationship between the peak area of the fraction having a smaller amount of positive charge adjacent to the fraction identified as the HbA0 of that sample, and the peak area of the carbamylated HbA0, is determined in advance. A predetermined factor (a) as a multiplying factor of the peak area of the former with respect to the peak area of the latter (in other words, the value obtained by dividing the peak area of the former by the peak area of the latter) is obtained from the correlation relationship. Then, a peak area corrected value as the peak area of carbamylated HbA0, is derived by dividing the peak area of the fraction having a smaller amount of positive charge adjacent to the fraction identified as HbA0, by the predetermined factor. Then, the remaining rate and the modification rate may be derived from the peak area corrected value. Further, for example, the sample of a healthy individual may be artificially aldehydated, and the correlation relationship between the peak area of the fraction having a smaller amount of positive charge adjacent to the fraction identified as the HbA0 of that sample, and the peak area of the aldehydated HbA0, may be determined in advance. A predetermined factor (a) as the multiplying factor of the peak area of the former with respect to the peak area of the latter is obtained from the correlation relationship. Then, a peak area corrected value as the peak area of aldehydated HbA0 may be derived by dividing the peak area of the fraction having a smaller amount of positive charge adjacent to the fraction identified as HbA0, by the predetermined factor. Then, the remaining rate and the modification rate may be derived from the peak area corrected value.

Note that, in an actual sample, cases in which carbamylation and aldehydation of HbA0 arise simultaneously are also possible. Therefore, there is little sense in distinguishing carbamylation from aldehydation. Thus, in the following description, the term "carbamylated HbA0 and/or aldehydated HbA0" is used both in cases in which carbamylation and aldehydation of HbA0 arise simultaneously, and in cases in which only one of carbamylation and aldehydation arises.

As described above, carbamylated HbA0 and/or aldehydated HbA0, which are chemically-modified HbA0, and labile A1c are detected in the same fraction. Therefore, if the remaining rate or modification rate of a sample that contains a large amount of labile A1c is derived from the peak area of a fraction including carbamylated HbA0 and/or aldehydated HbA0, there are cases in which the remaining rate is derived excessively (i.e., derived as being higher than it actually is). Further, if the proportion of stable A1c is corrected by using a remaining rate derived excessively, an accurate proportion of stable A1c cannot be derived. On the other hand, the fraction having a smaller amount of positive charge adjacent to the fraction identified as HbA0 does not include labile A1c. Therefore, the remaining rate or the modification rate is derived by using the peak area of the carbamylated HbA0 and/or aldehydated HbA0 derived from the fraction having a smaller amount of positive charge adjacent to the fraction identified as HbA0, and the proportion of stable A1c is derived by using the derived remaining rate. Thereby, even in a case in which a sample having a large amount of labile A1c is measured, the correction proportion of stable A1c can be derived in consideration of the proportion of chemically-modified stable A1c.

Note that it is thought that labile A1c being included in the same fraction as the fraction including carbamylated HbA0 and/or aldehydated HbA0 is because the molecular surface charges of carbamylated HbA0 and/or aldehydated HbA0 and labile A1c are close to each other. On the other hand, it is thought that labile A1c being included in a different fraction than a substance included in the fraction having a smaller amount of positive charge adjacent to the fraction identified as HbA0 is due to the fact that the molecular surface charge of labile A1c is sufficiently different from the surface charge of the substance included in the fraction having a smaller amount of positive charge adjacent to the fraction identified as HbA0. Further, the fraction having a smaller amount of positive charge adjacent to the fraction identified as HbA0 is thought to be a fraction including a substance also generated at the time when HbA0 is chemically modified. Further, the substance has a property of absorbing light of a wavelength of 415 nm. For these reasons, it is presumed that the substance is some type of hemoglobin compound.

The fraction having a smaller amount of positive charge adjacent to the fraction identified as HbA0 can also be referred to as the fraction that exists at a side, at which the positive charge amount is larger, of the fraction identified as stable A1c. In other words, the fraction can also be referred to as the fraction having a smaller amount of positive charge adjacent to the fraction identified as HbA0, and that exists at a side, at which the positive charge amount is larger, of the fraction identified as stable A1c. In other words, the fraction having a smaller amount of positive charge adjacent to the fraction identified as HbA0 can also be referred to as the fraction whose detection time is earlier than that of the fraction identified as HbA0. In other words, the fraction can also be referred to as the fraction whose detection time is later than that of the fraction identified as stable A1c. In other words, the fraction can also be referred to as the fraction whose detection time is earlier than that of the fraction identified as HbA0, and whose detection time is later than that of the fraction identified as stable A1c.

In the same way as described above in regard to the fraction including chemically-modified HbA0, for the peak area of the fraction having a smaller amount of positive charge adjacent to the fraction identified as HbA0, the numerical value itself may be used, or a numerical value corrected appropriately may be used. For example, in a case in which a component, which is other than a substance also generated at the time when HbA0 is chemically modified, is included in the fraction having a smaller amount of positive charge adjacent to the fraction identified as HbA0, the peak area, which is derived from the component other than the substance also generated at the time when HbA0 is chemically modified, is deducted from the peak area of the fraction. In a case in which the peak area derived from a component other than the substance also generated at the time when HbA0 is chemically modified is known, the known peak area may be deducted as a predetermined peak area. Further, samples of plural healthy individuals may be separated and analyzed, and a predetermined peak area as a statistical value of the peak area of a component other than a substance also generated at the time when HbA0 is chemically modified, may be determined in advance before measurement of the stable A1c of a sample. Then, when measuring the sample, the predetermined peak area may be deducted from the peak area of the fraction including chemically-modified HbA0. For example, the peak area corrected value as the statistical value is an average value or a median value or the like. Further, the aforementioned peak area corrected value may be derived on the basis of a value obtained by deducting the predetermined peak area value.

Next, the proportion of the peak area of the fraction including stable A1c, with respect to the entire peak area of the fractions including hemoglobin, is corrected by the remaining rate, from the time distribution of the hemoglobin obtained by separation analysis.

The entire peak area of the fractions including hemoglobin mentioned in the present specification can also be referred to as the value of the peak area corresponding to the total hemoglobin amount contained in the sample that is separated and analyzed. This can also be referred to as the total value of the peak area of the fractions derived from hemoglobin in the obtained time distribution of hemoglobin. Note that HbA0 accounts for a majority of the hemoglobin amount contained in the sample. Therefore, the entire peak area of the fractions including hemoglobin may be considered to be the same value as the peak area of the HbA0 fraction, and may be corrected. Further, a total value, which is derived so as to include the peak area of the HbA0 fraction and, in addition, the peak area of an adjacent fraction in the shape of the time distribution of hemoglobin, may be considered to be the entire peak area of the fractions including hemoglobin, and may be corrected.

Further, with regard to stable A1c as well, under the assumptions that the stable A1c is subjected to chemical modification at the modification rate at which the HbA0 was chemically modified, and that the stable A1c contained in the sample is the stable A1c that remains without having been chemically modified, the proportion of the peak area of the fraction including stable A1c with respect to the entire peak area of the fractions including hemoglobin is corrected by the remaining rate. In other words, the proportion, with respect to the entire peak area of the fractions including hemoglobin, of the total value of the peak area of the fraction including the stable A1c that remains without having been chemically modified and the peak area of the fraction including the stable A1c that was chemically modified, is derived by using the remaining rate. Due to this correction, a proportion of stable A1c that reflects the average blood sugar level over previous one to two months is derived.

For example, in a method of correcting the proportion of the peak area of the fraction including stable A1c with respect to the entire peak area of the fractions including hemoglobin by the remaining rate, the proportion of the peak area of the fraction including stable A1c with respect to the entire peak area of the fractions including hemoglobin may be divided by the remaining rate.

Note that the method of measuring stable A1c of the present disclosure preferably comprises: a step of distinguishing, whether or not a first proportion (ratio) is greater than or equal to a first threshold value, the first proportion representing a proportion of the peak area (D) of the second fraction, with respect to either the peak area (A) of the fraction including HbA0, or the entire peak area of the fractions including hemoglobin in the time distribution; and a step of, in a case in which the first proportion is greater than or equal to the first threshold value, correcting the peak area of the fraction including stable A1c using the correction rate.

Next is described the step of distinguishing, whether or not a first proportion is greater than or equal to a first threshold value, the first proportion representing a proportion of the peak area (D) of the second fraction, with respect to either the peak area (A) of the fraction including HbA0, or the entire peak area of the fractions including hemoglobin in the time distribution.

When hemoglobin within blood is separated and analyzed by a separation analysis method based on the principles of cation exchange as is the case with capillary electrophoresis, for example, the respective hemoglobins are detected in order from the hemoglobin having a small amount of positive charges to the hemoglobin having a large amount of positive charges. Specifically, the fraction including HbF is detected, and thereafter, the fractions including carbamylated HbA0, aldehydated HbA0 and labile A1c are detected. Thereafter, the fraction including stable A1c, the fraction adjacent to the fraction including HbA0, and the fraction including HbA0 are detected in this order. The fraction detected here including stable A1c is a fraction derived from the stable A1c that remains without having been chemically modified such as carbamylated or aldehydated. As described above, since carbamylated HbA0 or aldehydated HbA0 and labile A1c are detected in the same fraction, it cannot be judged, from the magnitude of the peak area of the fraction including carbamylated HbA0 or aldehydated HbA0, whether the sample contains carbamylated HbA0 or aldehydated HbA0, or whether the sample contains labile A1c. On the other hand, when the hemoglobin contained in the sample is artificially carbamylated or aldehydated, not only the peak area of the fraction including carbamylated HbA0 or aldehydated HbA0 and labile A1c, but also the peak area of the fraction having a smaller amount of positive charge adjacent to the fraction identified as HbA0, increase. Further, the fraction having a smaller amount of positive charge adjacent to the fraction identified as HbA0 does not include labile A1c. Therefore, it is judged whether or not the proportion of the peak area of the fraction (the second fraction) having a smaller amount of positive charge adjacent to the fraction identified as HbA0, with respect to either the peak area of the fraction including HbA0 or the entire peak area including hemoglobin of the time distribution of hemoglobin, is greater than or equal to the first threshold value. Thereby, it can suitably be distinguished whether or not the sample that is separated and analyzed is a sample containing a large amount of carbamylated HbA0 or aldehydated HbA0.

Note that it is thought that the reason why labile A1c is included in the same fraction as the fraction including carbamylated HbA0 or aldehydated HbA0 is that the molecular surface charges of carbamylated HbA0 or aldehydated HbA0 and labile A1c are close to each other. On the other hand, it is thought that the reason why labile A1c is included in a fraction different from a substance included in the fraction having a smaller amount of positive charge adjacent to the fraction identified as HbA0 is that the molecular surface charge of labile A1c is sufficiently different from the surface charge of the substance included in the fraction having a smaller amount of positive charge adjacent to the fraction identified as HbA0. Further, the fraction having a smaller amount of positive charge adjacent to the fraction identified as HbA0 is thought to be the fraction including a substance generated together with carbamylated HbA0 or aldehydated HbA0 at the time when HbA0 is carbamylated or aldehydated. The substance has a property of absorbing light of a wavelength of 415 nm. For these reasons, it is surmised that the substance is some type of hemoglobin compound.

The fraction having a smaller amount of positive charge adjacent to the fraction identified as HbA0 can also be referred to as the fraction that exists at a side, at which the positive charge amount is larger, of the fraction identified as stable A1c. In other words, the fraction can also be referred to as the fraction having a smaller amount of positive charge adjacent to the fraction identified as HbA0, and that exists at a side, at which the positive charge amount is larger, of the fraction identified as stable A1c. In other words, the fraction having a smaller amount of positive charge adjacent to the fraction identified as HbA0 can also be referred to as the fraction whose detection time is earlier than the fraction identified as HbA0. In other words, the fraction can also be referred to as the fraction whose detection time is later than the fraction identified as stable A1c. In other words, the fraction can also be referred to as the fraction whose detection time is earlier than the fraction identified as HbA0, and whose detection time is later than the fraction identified as stable A1c.

The HbA0 amount accounts for a majority of the total hemoglobin amount contained in blood. Therefore, the value of the entire peak area of the time distribution of the hemoglobin approximates the peak area of the fraction including HbA0. Accordingly, the present invention can be implemented appropriately even if the first proportion is derived by using either the peak area of the fraction including HbA0, or the entire peak area of the time distribution of the hemoglobin.

The first threshold value can be set appropriately. As described above, even if the sample is a sample that contains a large amount of labile A1c, the peak area of the fraction having a smaller amount of positive charge adjacent to the fraction identified as HbA0 is not large, and the extent of the carbamylation or the aldehydation of the HbA0 contained in the sample can be expressed appropriately. Here, for example, plural samples that have not been carbamylated or aldehydated, or samples at which the effects of chemical modification can be ignored, or samples of healthy individuals are collected and separated and analyzed, and the first threshold value may be determined from the first proportion obtained therefrom. For example, the maximum value of the first proportion obtained from plural samples may be used as the first threshold value, or a value greater than the maximum value may be used as the first proportion. In a case in which the fraction is greater than or equal to such a large value, it can be judged that the fraction has certainly been affected by carbamylation or aldehydation. In other words, if the first proportion is greater than or equal to the first threshold value that is such a large value, it can be thought the sample has certainly been affected by carbamylation or aldehydation. On the other hand, there are hardly any cases in which the first proportion of a sample that is not carbamylated nor aldehydated is greater than or equal to the first threshold value. Thereby, it is possible to avoid a sample, which contains a large amount of labile A1c, being wrongly judged to be a sample that contains a large amount of carbamylated HbA0 or aldehydated HbA0. Further, it is possible to avoid the correcting of a sample that does not require correction for the effects of having been carbamylated or aldehydated, and the proportion of stable A1c can be measured appropriately. Further, if strict distinction is not required, a value, which is smaller than the maximum value of the first proportions obtained from the plural samples, may be used as the first threshold value. For example, an average value or a median value or the like of the obtained first proportions may be used as the first threshold value. The first threshold value is, for example, 4% or more and preferably 9% or more.

Next, in a case in which the first proportion is greater than or equal to the first threshold value, the remaining rate, which is the proportion of the HbA0 that remains without having been chemically modified, is derived from the peak area of the fraction including chemically-modified HbA0 in the time distribution of hemoglobin, or from the peak area of the fraction having a smaller amount of positive charge adjacent to the fraction identified as HbA0. The value obtained by correcting, by the remaining rate, the proportion of the peak area of the fraction that contains stable A1c, with respect to the peak area of the fraction including HbA0 in the time distribution of the hemoglobin or with respect to the entire peak area of the fractions including hemoglobin, is used as the measured value of that fraction, i.e., the measured value of the fraction including stable A1c. The measured value is a value that has the significance of being the proportion that the stable A1c occupies in the entire hemoglobin amount.

Here, in a case in which the first proportion is less than the first threshold value, it may be considered that the sample is not affected by chemical modification, or that the effects of chemical modification are small enough to an extent of being able to be ignored, and it may be made such that correction by the aforementioned remaining rate is not carried out. In this case, the proportion of the peak area of the fraction including stable A1c, with respect to either the peak area of the fraction including HbA0 in the time distribution of the hemoglobin or the entire peak area of the fractions including hemoglobin, on which proportion correction by the remaining rate is not carried out, is used as the measured value of that fraction. The meaning of the measured value is as described previously. Further, both the proportion of the peak area that is not corrected by the remaining rate, and the proportion of the peak area corrected by the remaining rate, may be derived in advance, and a step may be carried out that distinguishes whether or not the first proportion is greater than or equal to the first threshold value, and, in a case in which the first proportion is less than the first threshold value, the proportion of the peak area that is not corrected by the remaining rate is used as the measured value.

In addition to the above-described step of distinguishing whether or not the first proportion is greater than or equal to the predetermined first threshold value, a step may be provided of distinguishing whether or not a second proportion (ratio), which is the proportion that the peak area of the fraction including chemically-modified HbA0 occupies in the peak area of the fraction including HbA0 or the entire peak area of the time distribution of the hemoglobin, is greater than or equal to a second threshold value, from the time distribution of the hemoglobin. By determining that the first proportion of the sample that is separated and analyzed is greater than or equal to the first threshold value, and that the magnitude of the peak area of the fraction having a smaller amount of positive charge adjacent to the stable A1c fraction also is greater than or equal to a given amount, it can be even more appropriately judged that the sample contains chemically-modified HbA0. In other words, if the sample is a sample at which the first proportion is greater than or equal to the first threshold value and the second proportion is greater than or equal to the second threshold value, it can be thought that that sample has certainly been affected by carbamylation or aldehydation. Further, in a case in which the first proportion is greater than or equal to the first threshold value and the second proportion is greater than or equal to the second threshold value, the proportion corrected by the above-described remaining rate may be used as the above-described measured value. The step of distinguishing whether or not the second proportion is greater than or equal to the second threshold value may be executed either before or after the step of distinguishing whether or not the first proportion is greater than or equal to the first threshold value.

As the second threshold value, for example, plural samples that have not been either carbamylated or aldehydated and are thought to have usual labile A1c amounts, may be collected and separated and analyzed, and the maximum value of the second proportions obtained therefrom may be used as the second threshold value. Further, for example, a value greater than the maximum value of the second proportions obtained from plural samples may be used as second threshold value. Further, in a case in which the distinction does not require high accuracy, an arbitrary value such as an average value or a median value of second proportions obtained from plural samples may be used as the second threshold value. The second threshold value can be made to be, for example, 3% or more of the total hemoglobin amount.

Further, a sample in which the second proportion is less than the second threshold value even if the first proportion is greater than or equal to the first threshold value, is understood to not contain chemically-modified HbA0, or to hardly contain any at all. Therefore, a proportion obtained by correcting, by the above-described remaining rate, the proportion of the peak area of the fraction including stable A1c, with respect to either the peak area of the fraction including HbA0 or the entire peak area including hemoglobin in the time distribution of the hemoglobin, is not used as the measured value. Further, the proportion of the peak area of the fraction including stable A1c, with respect to either the peak area of the fraction including HbA0 or the entire peak area of the time distribution of the hemoglobin, which proportion is not corrected by the remaining rate, is used as the measured value.

On the other hand, in a case in which the first proportion is greater than or equal to the first threshold value and the second proportion is greater than or equal to the second threshold value, a value obtained by correcting, by the remaining rate and as described above, the proportion of the peak area of the fraction including stable A1c, with respect to either the peak area of the fraction including HbA0 or the entire peak area of the time distribution of the hemoglobin, is used as the measured value.

[Analyzing System]

FIG. 1 shows a schematic configuration of an example of analyzing system A1 by which a method of measuring stable A1c of the present disclosure may be implemented. The analyzing system A1 is configured to have an analyzing device 1 and an analysis chip 2. The analyzing system A1 is a system that carries out separation analysis of hemoglobin, which is based on the principles of cation exchange, on the basis of the molecular surface charges of bloodstream hemoglobin by using specimen Sa, which is blood collected from a human body, as the subject. Hereinafter, the present invention will be described by using an analyzing system based on the principles of electrophoresis that utilizes the difference in the positive charge amounts of the molecular surfaces. However, the present invention is not limited to separation analysis based on the principles of electrophoresis.

<Preparation of Analysis Chip>

Figure 2:
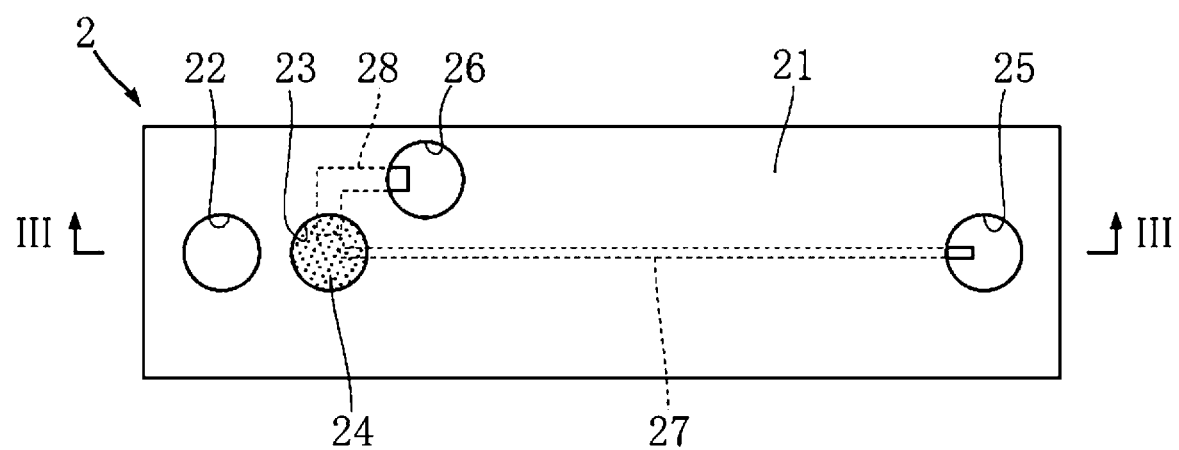
FIG. 2 is a plan view showing an analysis chip used in the analyzing system of FIG. 1.
Figure 3:
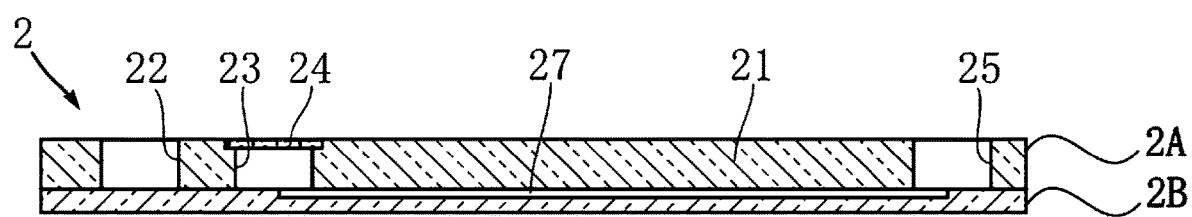
FIG. 3 is a cross-sectional view along line of FIG. 2.

The analysis chip 2 retains the specimen Sa, and, in a state of being loaded in the analyzing device 1, provides a site for the analysis of the subject that is the specimen Sa. In the present embodiment, the analysis chip 2 is configured as a so-called disposable analysis chip, and is intended to be disposed of after a single analysis is completed. As shown in FIG. 2 and FIG. 3, the analysis chip 2 has a main body 21, a mixing reservoir 22, an introducing reservoir 23, a filter 24, a discharge reservoir 25, an electrode reservoir 26, a capillary channel 27, and a connecting flow path 28. FIG. 2 is a plan view of the analysis chip 2, and FIG. 3 is a cross-sectional view along line in FIG. 2. Note that the analysis chip 2 is not limited to a disposable type chip, and may be a chip used over plural analyses. Further, the analyzing system of the present embodiment is not limited to a configuration in which the analysis chip 2 that is a separate body is loaded into the analyzing device 1, and may be a configuration in which a functional region, which exhibits a function similar to that of the analysis chip 2, is integrated into the analyzing device 1.

The main body 21 is a base of the analysis chip 2. The material thereof is not particularly limited, and glass, fused silica, plastic and the like are examples thereof. In the present embodiment, the main body 21 has a configuration in which an upper side portion 2A and a lower side portion 2B in FIG. 3 are formed as separate bodies, and these are joined together. Note that the present disclosure is not limited to this configuration, and, for example, the main body 21 may be formed integrally.

The mixing reservoir 22 is an example of a site at which a mixing step described later, in which the specimen Sa and a dilution liquid Ld are mixed, is carried out. The mixing reservoir 22 is configured, for example, as a concave portion that opens upwardly by a through-hole formed in an upper side portion 2A of the main body 21. The introducing reservoir 23 is a reservoir into which a mixed specimen Sm as a sample solution is introduced, the mixed specimen Sm being obtained by the mixing step in the mixing reservoir 22. The introducing reservoir 23 is configured, for example, as a concave portion that opens upwardly by a through-hole formed in the upper side portion 2A of the main body 21.

The filter 24 is provided at an opening portion of the introducing reservoir 23 as an example of a path of introduction into the introducing reservoir 23. The exact configuration of the filter 24 is not limited, and, for example, a cellulose acetate film filter (manufactured by Advantec, and having a hole diameter of 0.45 µm) is a suitable example.

The discharge reservoir 25 is a reservoir positioned at a downstream side of an electro-osmotic flow in the electrophoresis. The discharge reservoir 25 is configured, for example, as a concave portion that opens upwardly by a through-hole formed in the upper side portion 2A of the main body 21. The electrode reservoir 26 is a reservoir into which an electrode 31 is inserted in an analysis step in accordance with electrophoresis. The electrode reservoir 26 is configured, for example, as a concave portion that opens upwardly by a through-hole formed in the upper side portion 2A of the main body 21. The connecting flow path 28 connects the introducing reservoir 23 and the electrode reservoir 26, and configures a conduction path between the introducing reservoir 23 and the electrode reservoir 26.

The capillary channel 27 is a minute flow path that connects the introducing reservoir 23 and the discharge reservoir 25, and is a site at which the electro-osmotic flow (EOF) in the electrophoresis arises. The capillary channel 27 is, for example, configured as a groove formed in a lower side portion 2B. Note that concave portions or the like, which are for promoting an illumination of light onto the capillary channel 27 and an emission of light through the capillary channel 27, may be formed appropriately in the main body 21. The size of the capillary channel 27 is not particularly limited, but, as an example, a width thereof is 25 µm to 100 µm, and a depth thereof is 25 µm to 100 µm, and a length thereof is 5 mm to 150 mm. An overall size of the analysis chip 2 is appropriately set in accordance with the size of the capillary channel 27, and the sizes and the arrangement of the mixing reservoir 22, the introducing reservoir 23, the discharge reservoir 25 and the electrode reservoir 26, and the like.

Note that the analysis chip 2 of the above-described configuration is an example, and any analysis chip of a configuration by which an analysis by electrophoresis is possible can be suitably employed.

<Analyzing Device>

The analyzing device 1 carries out analyzing processing with the specimen Sa as a subject, in a state in which the analysis chip 2 on which the specimen Sa is spotted is loaded in the analyzing device 1. As shown in FIG. 1, the analyzing device 1 has electrodes 31, 32, a light source 41, an optical filter 42, a lens 43, a slit 44, a detector 5, a dispenser 6, a pump 61, a dilution liquid reservoir 71, a migration liquid reservoir 72 and a control unit 8. Note that the light source 41, the optical filter 42, the lens 43 and the detector 5 provide an example of what is called a measuring section in the present invention.

The electrode 31 and the electrode 32 are for applying a predetermined voltage to the capillary channel 27 in the electrophoresis step. The electrode 31 is inserted in the electrode reservoir 26 of the analysis chip 2, and the electrode 32 is inserted in the discharge reservoir 25 of the analysis chip 2. The voltage applied between the electrode 31 and the electrode 32 is not particularly limited, and is, for example, 0.5 kV to 20 kV.

The light source 41 is a region that emits light for measuring the absorbance as an optical measured value in the electrophoresis. The light source 41 has, for example, an LED chip that emits light of a predetermined wavelength range. The optical filter 42 attenuates light of a predetermined wavelength among the light from the light source 41, and transmits light of other wavelengths. The lens 43 focuses the light transmitted through the optical filter 42, onto a site of analysis of the capillary channel 27 of the analysis chip 2. The slit 44 is for removing excess light that can give rise to scattering or the like, among the light focused by the lens 43. Note that the light source 41 can be selected appropriately in accordance with principles of detecting hemoglobin. In a case in which absorbance is measured, the light source 41 that can emit the absorption wavelength of hemoglobin is selected. Further, in a case in which the hemoglobin is detected by fluorescent light or emitted light, the light source 41 that can emit excitation light is selected.

The detector 5 receives the light from the light source 41 transmitted through the capillary channel 27 of the analysis chip 2, and is configured so as to have, for example, photodiodes or a photo IC or the like. In the same way as the light source 41, the detector 5 also can be selected appropriately in accordance with principles of detecting hemoglobin.

In this way, the path by which the light emitted from the light source 41 reaches the detector 5 is referred to as an optical path. Further, the optical measured value of the solution (i.e., either the specimen solution or the migration liquid, or a mixed solution thereof), which flows through the capillary channel 27 at the position where the optical path intersects the capillary channel 27, is measured. Namely, the position of the capillary channel 27 intersected by the optical path from the light source 41 to the detector 5 is a measuring section of the optical measured value. Absorbance is an example of the optical measured value. The absorbance expresses the proportion of the light in the optical path absorbed by the solution flowing through the capillary channel 27, and expresses an absolute value of a common logarithmic value of a ratio of an incident light intensity and a transmitted light intensity. In this case, a spectrophotometer for general purpose can be used as the detector 5. Note that absorbance does not have to be used, and any value provided that it is an optical measured value, such as simply the value of the transmitted light intensity itself or the like, can be used in the present invention. Hereinafter, a case in which absorbance is used as the optical measured value is described as an example.

The dispenser 6 dispenses predetermined amounts of the dilution liquid Ld or the migration liquid Lm and the mixed specimen Sm, and includes a nozzle, for example. The dispenser 6 can be moved between plural predetermined positions in the analyzing device 1 by an unillustrated driving mechanism. The pump 61 is an aspiration source and the discharge source with respect to the dispenser 6. The pump 61 may also be used as the aspiration source and the discharge source of unillustrated ports provided at the analyzing device 1. These ports are used to fill of the migration liquid Lm and the like. Further, a pump for an exclusive use that is separate from the pump 61 may be provided.

The dilution liquid reservoir 71 is a reservoir for storing the dilution liquid Ld. The dilution liquid reservoir 71 may be a reservoir provided permanently at the analyzing device 1, or a container in which a predetermined amount of the dilution liquid Ld is sealed may be loaded into the analyzing device 1. The migration liquid reservoir 72 is a reservoir for storing the migration liquid Lm. The migration liquid reservoir 72 may be a reservoir provided permanently at the analyzing device 1, or a container in which a predetermined amount of the migration liquid Lm is sealed may be loaded into the analyzing device 1.

Figure 4:
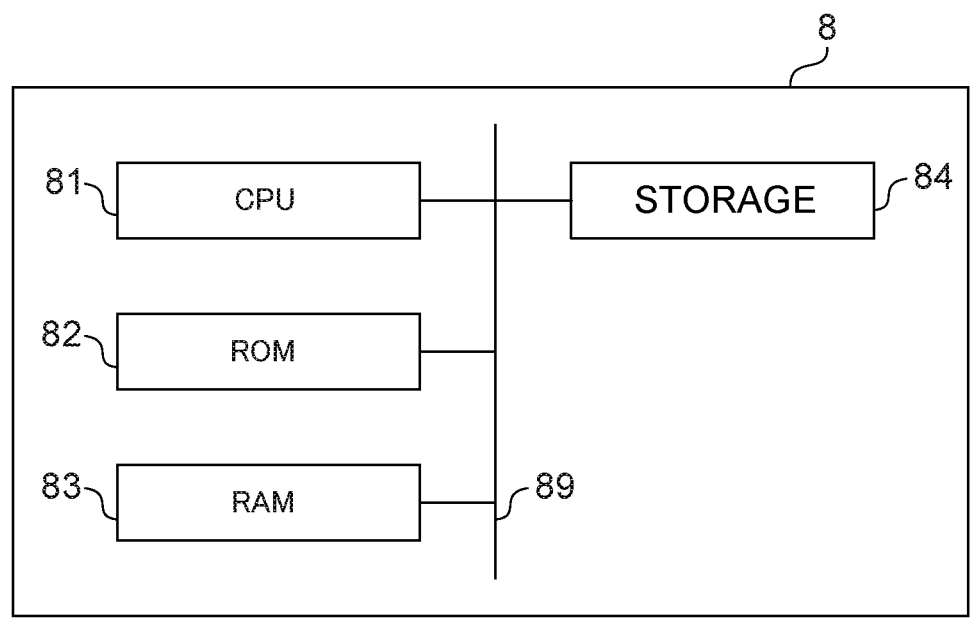
FIG. 4 is a block drawing showing a hardware configuration of a control unit.

The control unit 8 controls the respective members at the analyzing device 1. As shown by a hardware configuration in FIG. 4, the control unit 8 has a CPU (Central Processing Unit) 81, a ROM (Read Only Memory) 82, a RAM (Random Access Memory) 83, and a storage 84. The respective members are connected via a bus 89 so as to be able to communicate with one another.

The CPU 81 is the central computing processing unit, and executes various types of programs and controls the respective sections. Namely, the CPU 81 reads a program out from the ROM 82 or the storage 84, and executes the program by using the RAM 83 as a workspace. The CPU 81 carries out control of the above-described respective members and carries out various types of computing processings, in accordance with the programs recorded in the ROM 82 or the storage 84.

The ROM 82 stores various types of programs and various types of data. The RAM 83, as a workspace, temporarily stores programs and data. The storage 84 is configured by an HDD (Hard Disk Drive), an SSD (Solid State Drive) or a flash memory, and stores various types of programs, including an operating system, and various types of data. In the present aspect, the programs and the various data that relate to measurement and judgment are stored in the ROM 82 or the storage 84. Further, measurement data can be stored in advance in the storage 84 as well.

Figure 5:
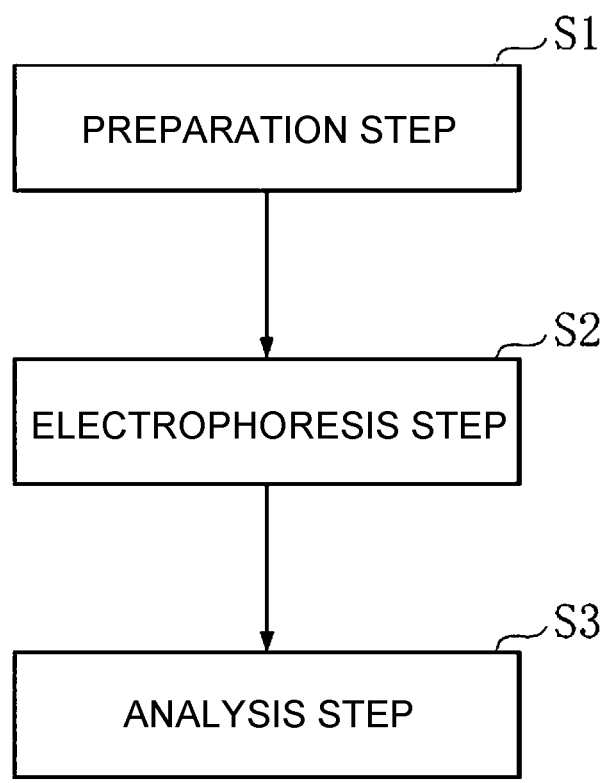
FIG. 5 is a flowchart showing an analyzing method.

The control unit 8 executes respective steps shown in FIG. 5 at the analyzing device 1, due to, among the above-described a hardware configuration, the CPU 81 executing the aforementioned programs. Details of these steps are described later.

<Preparation of Dilution Liquid, Migration Liquid and Mixed Specimen>

The dilution liquid Ld, by being mixed with the specimen Sa, generates the mixed specimen Sm as a specimen solution. A main agent of the dilution liquid Ld is not particularly limited, and water and saline are examples thereof, and liquids of components similar to those of the migration liquid Lm described hereinafter are preferable examples thereof. Further, in addition to the aforementioned main agent, additives may be added as needed to the dilution liquid Ld.

The migration liquid Lm is a medium that, in the step of analyzing in accordance with electrophoresis, is filled into the discharge reservoir 25 and the capillary channel 27, and generates the electro-osmotic flow in the electrophoresis. The migration liquid Lm is not particularly limited, but a liquid that employs an acid is desirable. The acid is, for example, citric acid, maleic acid, tartaric acid, succinic acid, fumaric acid, phthalic acid, malonic acid, or malic acid. Further, it is preferable that the migration liquid Lm contain a weak base. Examples of the weak base are arginine, lysine, histidine, tris and the like. The pH of the migration liquid Lm is in a pH range of 4.5 to 6, for example. MES, ADA, ACES, BES, MOPS, TES, HEPES and the like are types of buffers of the migration liquid Lm. Further, in the same way as mentioned in the description of the dilution liquid Ld, additives may be added to the migration liquid Lm as needed.

The following migration liquid Lm, dilution liquid Ld and mixed specimen Sm are examples, but these can be selected arbitrarily provided that there is a combination that gives rise to a change in the optical measured value due to the arrival of the interface between the specimen solution (the mixed specimen Sm) and the migration liquid Lm, at the interface arrival point in time described later.

<Preparation Step, Electrophoresis Step, Analyzing Step>

Next, an example of separation analysis of hemoglobin carried out by using the analyzing system A1 is described hereinafter. FIG. 5 is a flowchart showing the hemoglobin separation analysis method of the present embodiment. The present separation analysis method has a preparation step S1, an electrophoresis step S2, and an analysis step S3.

<Preparation Step S1>

Figure 6:
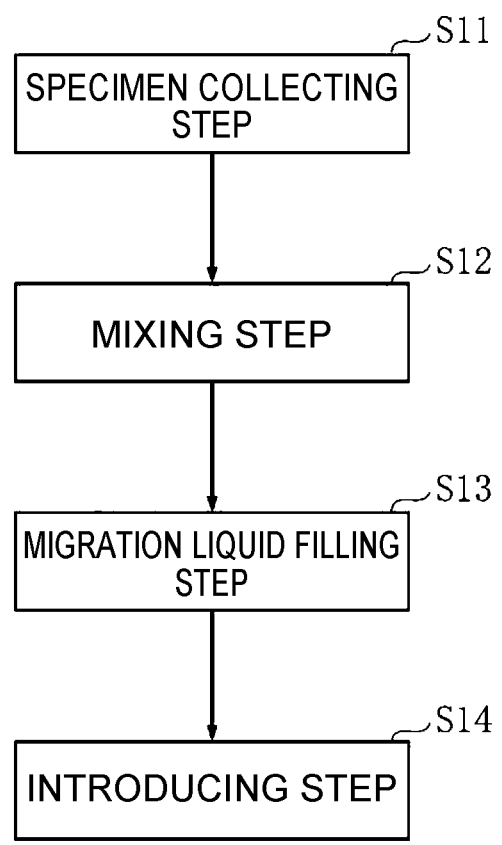
FIG. 6 is a flowchart showing processes of a preparation step.

FIG. 6 is a flowchart showing the processes of the preparation step S1. In the present embodiment, as shown in FIG. 6, the preparation step S1 has a specimen collecting step S11, a mixing step S12, a migration liquid filling step S13, and an introducing step S14.

<Specimen Collecting Step S11>

First, the specimen Sa is readied. In the present embodiment, the specimen Sa is blood collected from a human body. The blood may be whole blood, component-separated blood, or hemolyzed blood, or the like. Then, the analysis chip 2, onto which the specimen Sa is dispensed, is loaded into the analyzing device 1.

<Mixing Step S12>

Figure 7:
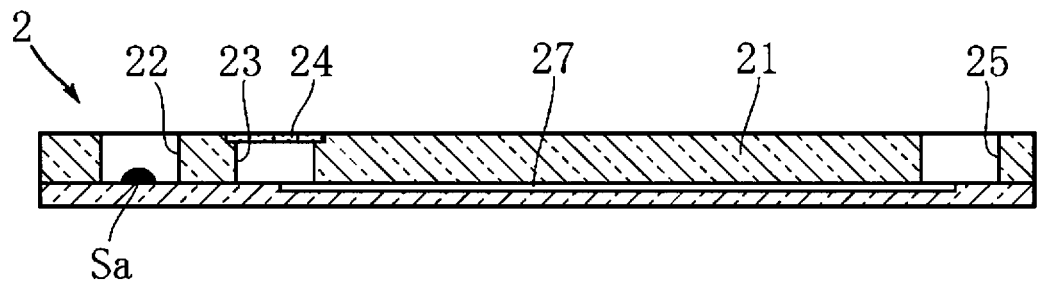
FIG. 7 is a cross-sectional view showing a step of the preparation step of FIG. 6.
Figure 8:
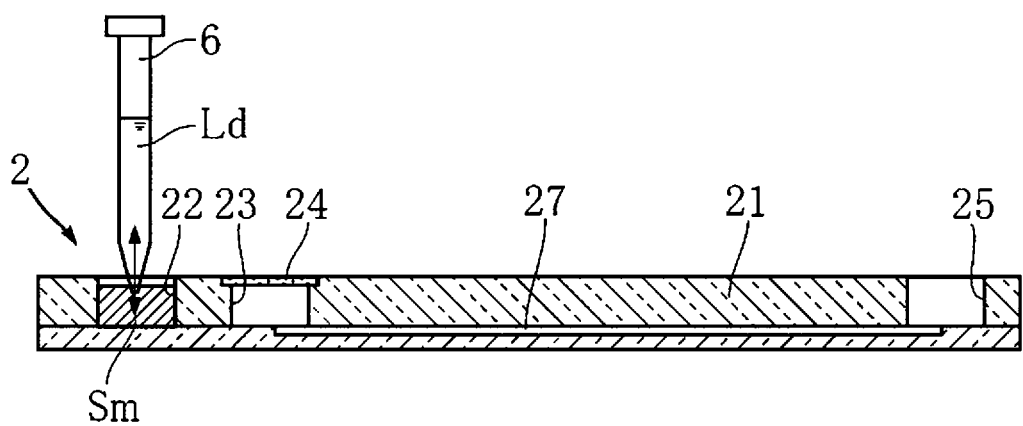
FIG. 8 is a cross-sectional view showing a step of the preparation step of FIG. 6.

Next, the specimen Sa and the dilution liquid Ld are mixed together. As shown in FIG. 7, a predetermined amount of the specimen Sa is spotted into the mixing reservoir 22 of the analysis chip 2. Next, a predetermined amount of the dilution liquid Ld of the dilution liquid reservoir 71 is aspirated by the dispenser 6, and, as shown in FIG. 8, the predetermined amount of the dilution liquid Ld is dispensed into the mixing reservoir 22 of the analysis chip 2. Then, by using the pump 61 as the aspiration source and the discharge source, aspiration and discharge of the dilution liquid Ld from the dispenser 6 are repeated. Thereby, at the mixing reservoir 22, the specimen Sa and the dilution liquid Ld are mixed-together, and a mixed specimen Sm as a specimen solution is obtained. The mixing of the specimen Sa and the dilution liquid Ld may be carried out by a method other than drawing-in and purging by the dispenser 6.

<Migration Liquid Filling Step S13>

Figure 9:
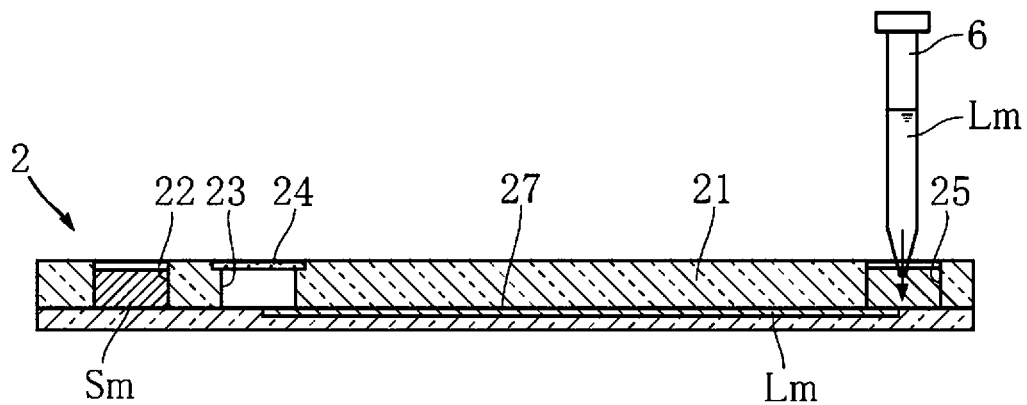
FIG. 9 is a cross-sectional view showing a step of the preparation step of FIG. 6.

Next, a predetermined amount of the migration liquid Lm of the migration liquid reservoir 72 is aspirated by the dispenser 6, and, as shown in FIG. 9, the predetermined amount of the migration liquid Lm is dispensed into the discharge reservoir 25 of the analysis chip 2. Then, the opening at an upper side of the discharge reservoir 25 is covered by the aforementioned port, and the migration liquid Lm is filled into the discharge reservoir 25 and the capillary channel 27 by a method such as appropriate discharge and aspiration of air from the port to the discharge reservoir 25 interior, or the like.

<Introducing Step S14>

Figure 10:
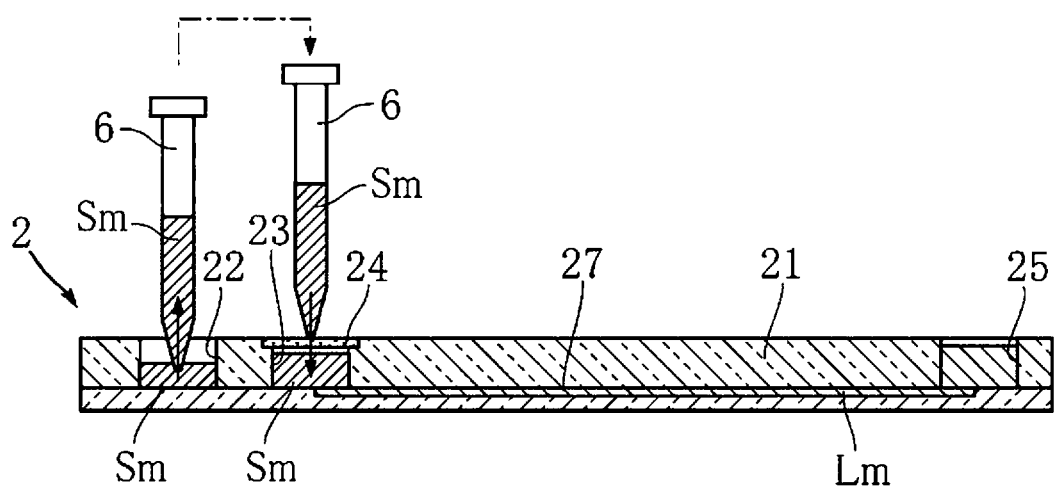
FIG. 10 is a cross-sectional view showing a step of the preparation step of FIG. 6.

Next, as shown in FIG. 10, a predetermined amount of the mixed specimen Sm is collected from the mixing reservoir 22 by the dispenser 6. Then, the predetermined amount of the mixed specimen Sm is introduced into the introducing reservoir 23 from the dispenser 6. In the introduction, the mixed specimen Sm passes through the filter 24 provided at the opening portion of the introducing reservoir 23 that is an example of the path of introduction into the introducing reservoir 23. Further, in the present embodiment, the mixed specimen Sm is filled from the introducing reservoir 23 through the connecting flow path 28 into the electrode reservoir 26. At this time, flowing of the mixed specimen Sm from the introducing reservoir 23 via the connecting flow path 28 to the electrode reservoir 26 occurs. However, from the introducing reservoir 23 to the connecting flow path 28, the mixed specimen Sm flows in a direction that is substantially orthogonal to the length direction of the capillary channel 27 (see FIG. 2). On the other hand, the migration liquid Lm of the capillary channel 27 hardly moves at all at this stage. As a result, due to shear flow arising at the connected portion of the introducing reservoir 23 and the capillary channel 27 (see FIG. 3), there occurs a state in which a distinct interface arises between the mixed specimen Sm and the migration liquid Lm. Note that, provided that it is a method by which an interface arises between the mixed specimen Sm and the migration liquid Lm, any means can be employed such as physically providing a movable filter at a border between the introducing reservoir 23 and the capillary channel 27, or changing the method of flowing by control, or the like.

<Electrophoresis Step S2>

Next, the electrode 31 (see FIG. 1) is inserted in the electrode reservoir 26 (see FIG. 2), and the electrode 32 (see FIG. 1) is inserted in the discharge reservoir 25. Subsequently, a voltage is applied to the electrode 31 and the electrode 32 in accordance with an instruction from the control unit 8. The voltage is, for example, 0.5 kV to 20 kV. Thereby, an electro-osmotic flow is generated, and the mixed specimen Sm is gradually moved within the capillary channel 27 from the introducing reservoir 23 to the discharge reservoir 25. At this time, since the mixed specimen Sm is filled with the introducing reservoir 23, hemoglobin (Hb) that is the above-described analysis component is electrophoresed in a state in which the mixed specimen Sm is being continuously supplied at the capillary channel 27. At this time, the mixed specimen Sm migrates through the capillary channel 27 while pushing the migration liquid Lm in a downstream direction, while the state in which the above-described interface is maintained between the mixed specimen Sm and the migration liquid Lm remains as is. Then, the emitting of light from the light source 41 is started, and measurement of the absorbance by the detector 5 is carried out. Then, the relationship between the absorbance and the time that has elapsed from the start of application of voltage from the electrode 31 and the electrode 32 is measured.

<Analysis Step S3>

Figure 11A:
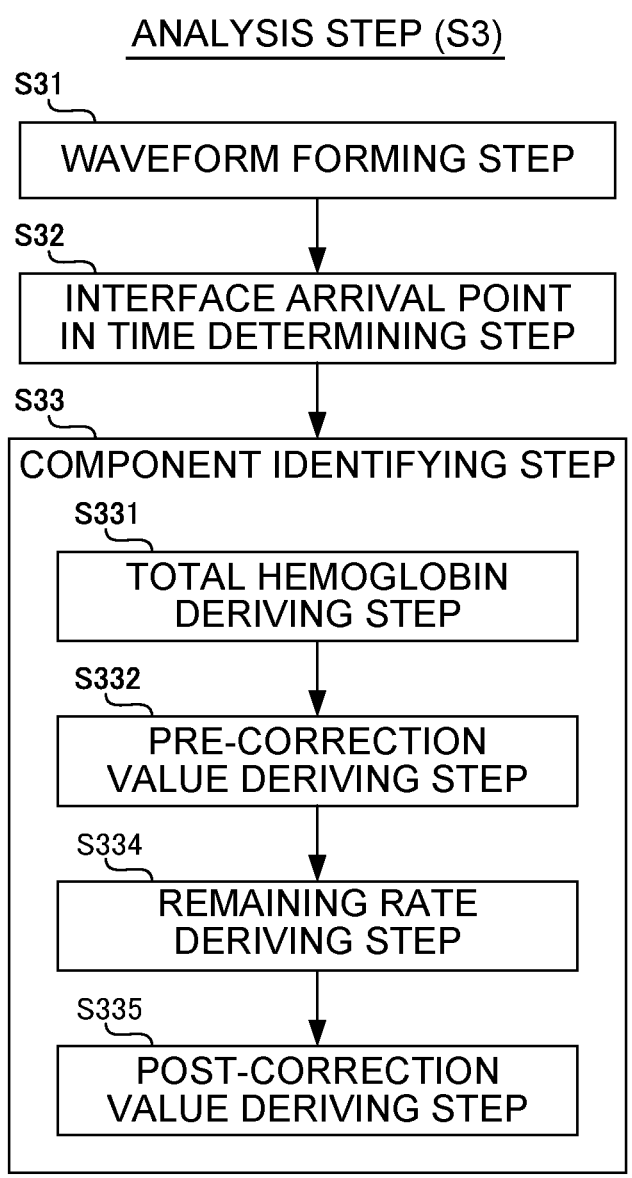
FIG. 11A is a flowchart showing processes of an analysis step.

Here, the absorbance peak, which corresponds to a component having a relatively fast moving speed within the mixed specimen Sm (in other words, a component in which the positive charge amount of the molecular surfaces is relatively small), appears at a point in time when the elapsed time from the aforementioned start of application of the voltage is relatively short. On the other hand, the absorbance peak, which corresponds to a component having a relatively slow moving speed within the mixed specimen Sm (in other words, a component in which the positive charge amount of the molecular surfaces is relatively large), appears at a point in time when the elapsed time from the aforementioned start of application of voltage is relatively long. Analysis (separation and measurement) of the components within the mixed specimen Sm is carried out by utilizing this. The analysis step S3 shown in FIG. 11A is executed by control of the control unit 8 on the basis of the measured absorbances. The analysis step S3 of the present embodiment includes a waveform forming step S31, an interface arrival point in time determining step S32, and a component identifying step S33.

<Waveform Forming Step S31>

Figure 12:
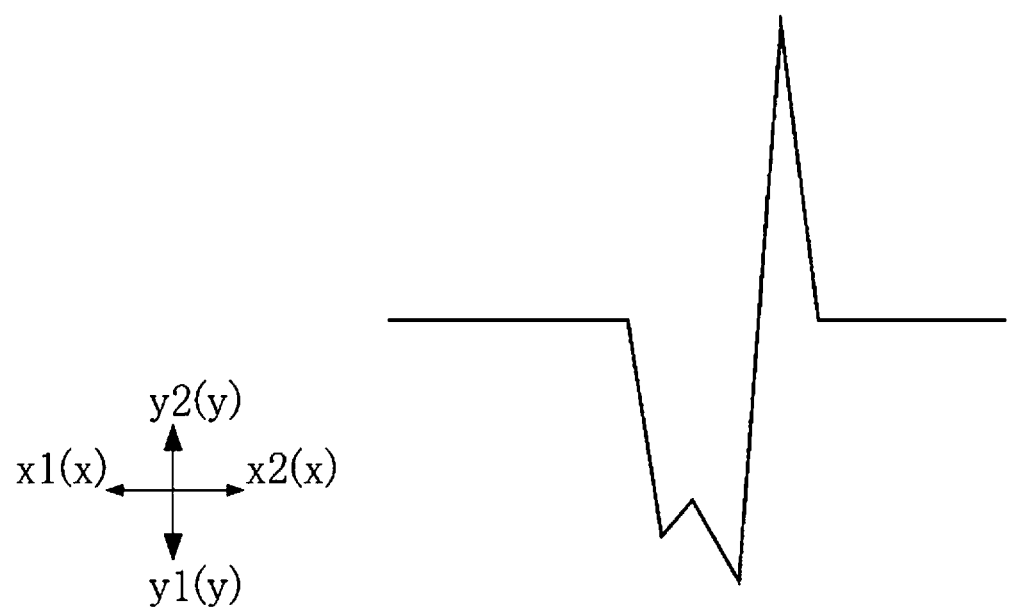
FIG. 12 is a graph showing an example of waveform data formed by a waveform forming step.

In the present step, an electropherogram is prepared by the control unit 8 carrying out computing processing on the measured absorbances. Here, the voltage application start time is used as the measurement start time, and an electropherogram as a measured waveform that relates to the absorbance and that expresses a change in the optical measured value corresponding to the time elapsed from after the aforementioned start of measurement, is formed. Specifically, a waveform of the differential values is formed by differentiating the measured absorbance over time. FIG. 12 shows an example of a differential waveform formed by differentiating absorbance over time. The x-axis in the drawing is a time axis, and the y-axis is a differential value axis. In the following drawings and explanation, a negative direction side along the time axis x is direction x1 side, and a positive direction side is direction x2 side. A negative direction side along the differential value axis y is direction y1 side, and a positive direction side is direction y2 side.

<Interface Arrival Point in Time Determining Step S32>

Figure 13:
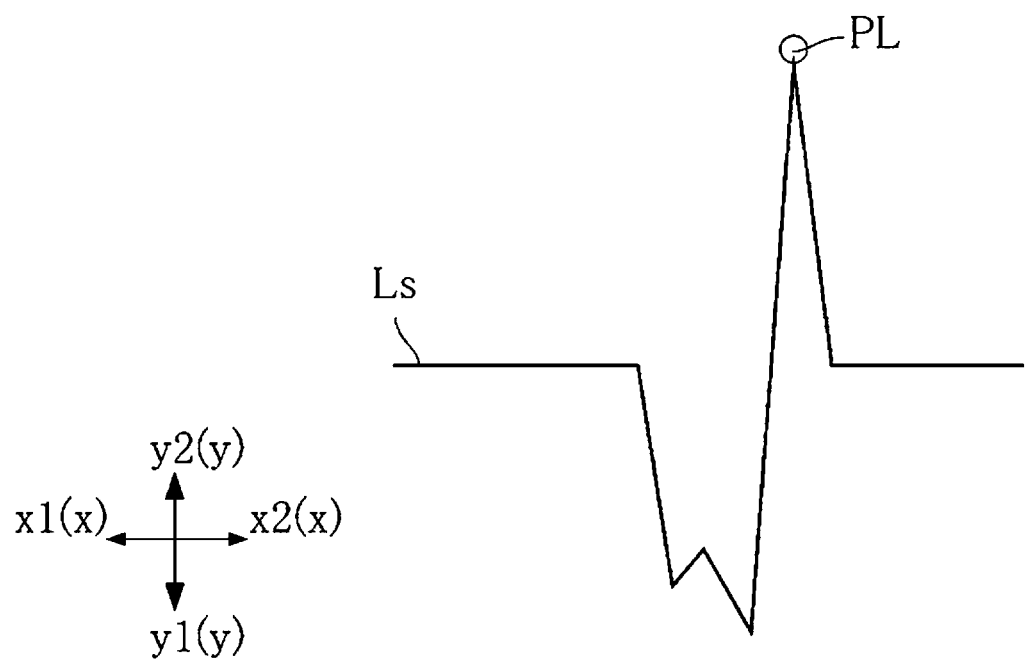
FIG. 13 is a graph showing the determination of a furthest point.

The present step is a step of determining an interface arrival point in time which is a point in time at which an interface between the mixed specimen Sm and the migration liquid Lm migrating in the downstream direction of the capillary channel due to the application of the voltage, arrives at the detector 5. The interface between the mixed specimen Sm and the migration liquid Lm is a peak that appears first after the start of electrophoresis. The peak of the interface of the mixed specimen Sm and the migration liquid Lm is shown in FIG. 13. As shown in FIG. 13, among the peak expressed by the interface of the mixed specimen Sm and the migration liquid Lm, the point, at which the differential value is furthest away from a reference value Ls in the electropherogram, is determined. In the illustrated example, the point apart from the reference value Ls in direction y2 is the furthest apart from the reference value Ls, and the point is determined as a furthest point PL. Here, a point in time at which the application of the voltage starts in the above-described electrophoresis step S2 is 0, and the point in time when the furthest point PL is detected is the interface arrival point in time.

<Component Identifying Step S33>

Figure 14:
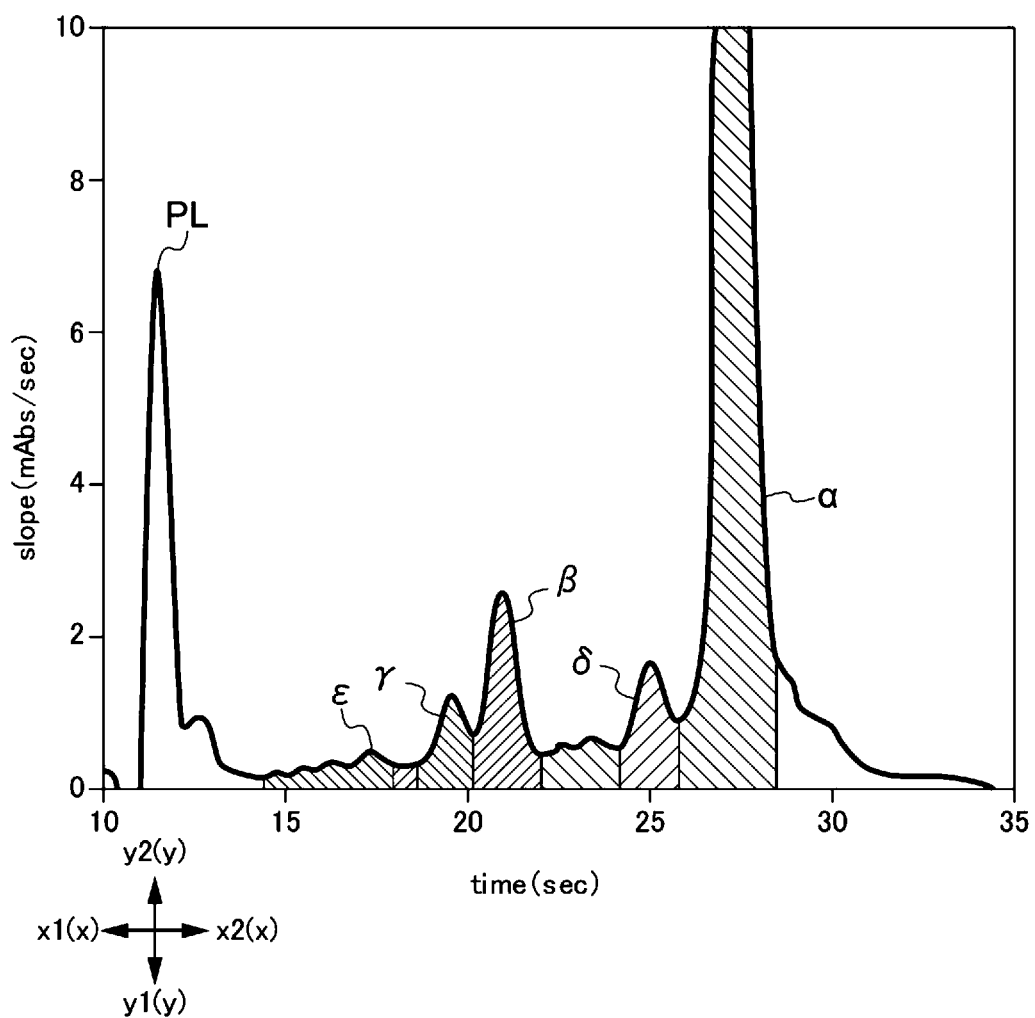
FIG. 14 shows an example of an electropherogram of hemoglobin.

An example of the differential waveform after the interface arrival point in time, which is obtained in the above-described waveform forming step S31, is shown in FIG. 14. In the drawing, the x-axis shows a migration time period (unit: sec) with a point in time at which application of the voltage is started being 0, and the y-axis shows a slope value (unit: mAbs/sec) that is a value obtained by time-differentiating the absorbance. Further, the peak in the vicinity of a migration time of 11.5 seconds is the furthest point PL shown in FIG. 13, and the point in time is the interface arrival point in time. Further, in the present step, hemoglobin components are specified from the differential waveform. A fraction α that has a maximum peak after the interface arrival point in time is identified as HbA0. Then, for each peak that appears from the interface arrival point in time to the peak of HbA0, the component expressed by each peak is identified by a ratio of a time period from the interface arrival point in time to a detection time of each peak, with respect to the time period from the interface arrival point in time to the time when the peak of the HbA0 is detected. For example, in FIG. 14, the peak (fraction β) that indicates stable A1c (S-A1c) is identified in this way.

The amount of each component is derived from the respective peaks identified in this way. Specifically, a peak identified as a given component is a maximum value, and an area of a fraction including the maximum value can be used as an amount of the component corresponding to the peak. Here, both ends of the fraction can be set appropriately, and, for example, the both ends may be made to be minimum values at either side of the maximum value.

In this way, the entire peak area of the fractions including hemoglobin is derived in the total hemoglobin deriving step shown in S331. Here, the HbA0 amount accounts for a majority of a total hemoglobin amount. Therefore, an entire peak area of fractions including hemoglobin may be an area derived at only the HbA0 fraction, or may be based on an area including the HbA0 fraction and fractions at a periphery thereof, or may be an entire area of a region attributed to hemoglobin within the electropherogram. None of these cases greatly affect calculation of a pre-correction value (X) and a post-correction value (Y) described later.

Next, in a pre-correction value deriving step shown in S332, a pre-correction value (X) is derived by deriving a proportion of a peak area of a fraction including stable A1c, with respect to the entire peak area of the fractions including hemoglobin. The peak area of the fraction including stable A1c used in deriving the pre-correction value (X) is determined as an area of fraction β between minimum values at both ends of the S-A1c peak shown in FIG. 14. Namely, the peak area of fraction β including stable A1c is a peak area derived from the stable A1c that remains without having been chemically modified. Therefore, the pre-correction value (X) is a proportion of the peak area of the fraction including the stable A1c that remains without having been chemically modified, with respect to the entire peak area of the fractions including hemoglobin. In other words, this can also be referred to as a proportion of the peak area that does not take chemically-modified stable A1c into consideration.

Next, in the remaining rate deriving step shown in S334, modification rate (P), which is a proportion of a peak area including chemically-modified HbA0 with respect to the total value of the peak area of the fraction including HbA0 and the peak area of the fraction including chemically-modified HbA0, is derived. Then, remaining rate (Q), which is a proportion of HbA0 with respect to the total value of the peak area of the fraction including HbA0 and the peak area of the fraction including chemically-modified HbA0, is derived from the modification rate (P).

As shown in Examples described later, it is thought that at least one of carbamylated HbA0 or aldehydated HbA0 are included in fraction γ (the first fraction), which is in the vicinity of a migration time of 19 seconds and is a fraction adjacent at an earlier side, i.e., at a side at which the positive charge amount is smaller, to the fraction of stable A1c. In the remaining rate deriving step S334, the proportion (G/(A+G)) of the fraction γ, with respect to the total value of the peak area (A) of the fraction including HbA0 and the peak area (G) of the fraction including chemically-modified HbA0, is used as the modification rate (P). Note that, as described above, a majority of a total value of the peak area of fraction γ and the peak area of the fraction including HbA0 is occupied by the peak area of the fraction including HbA0. Therefore, a proportion of the peak area (G) of fraction γ with respect to the peak area of the fraction including HbA0 may be derived, and this may be used as the modification rate (P). Further, since the peak area of the fraction including HbA0 approximates the peak area corresponding to the total hemoglobin contained in the sample, the proportion of the peak area of fraction γ with respect to the entire peak area of the fractions including hemoglobin may be derived and used as the modification rate (P).

On the other hand, it can be thought that fraction δ (the second fraction), which is in the vicinity of a migration time of 25 seconds and is a fraction adjacent at an earlier side than the HbA0 fraction, i.e., at a side at which a positive charge amount is smaller, includes a substance generated together with chemically-modified HbA0 at the time when HbA0 is carbamylated or aldehydated. In the remaining rate deriving step S334, as described above, the peak area (G) of the fraction including chemically-modified HbA0 may be derived from a peak area (D) of the fraction δ, and the modification rate (P) may be derived. Specifically, a proportion of the peak area of the fraction including chemically-modified HbA0 and is derived from the fraction δ, with respect to the total value of the peak area of the fraction including HbA0 and the peak area of the fraction including chemically-modified HbA0 and is derived from the fraction δ, may be derived, and the modification rate (P) may be derived. Note that, as described above, the majority of the total value of the peak area of the fraction including chemically-modified HbA0 and the peak area of the fraction including HbA0 is occupied by the peak area of the fraction including HbA0. Therefore, the proportion of the peak area of chemically-modified HbA0 derived from the fraction δ, with respect to the peak area of the fraction including HbA0, may be derived, and may be used as the modification rate (P). Further, since the peak area of the fraction including HbA0 is near the peak area that corresponds to the total hemoglobin contained in the sample, the proportion of the peak area of chemically-modified HbA0 derived from fraction δ, with respect to the entire peak area of the fractions including hemoglobin, may be derived and used as the modification rate (P).

Further, a remaining rate (Q) is derived by subtracting the derived modification rate (P) from 1. Note that the derivation of the remaining rate (Q) is not limited to this method of derivation.

Then, in a post-correction value deriving step shown in S335, post-correction value (Y), which is a proportion of the total value of the peak area of the fraction that contains the stable A1c that remains without having been chemically modified and the peak area of the fraction including chemically-modified A1c, with respect to the entire peak area of the fractions including hemoglobin, is derived from the pre-correction value (X) and the remaining rate (Q) that were derived as described above. Specifically, the post-correction value (Y) is derived by dividing the pre-correction value (X) by the remaining rate (Q).

Figure 11B:
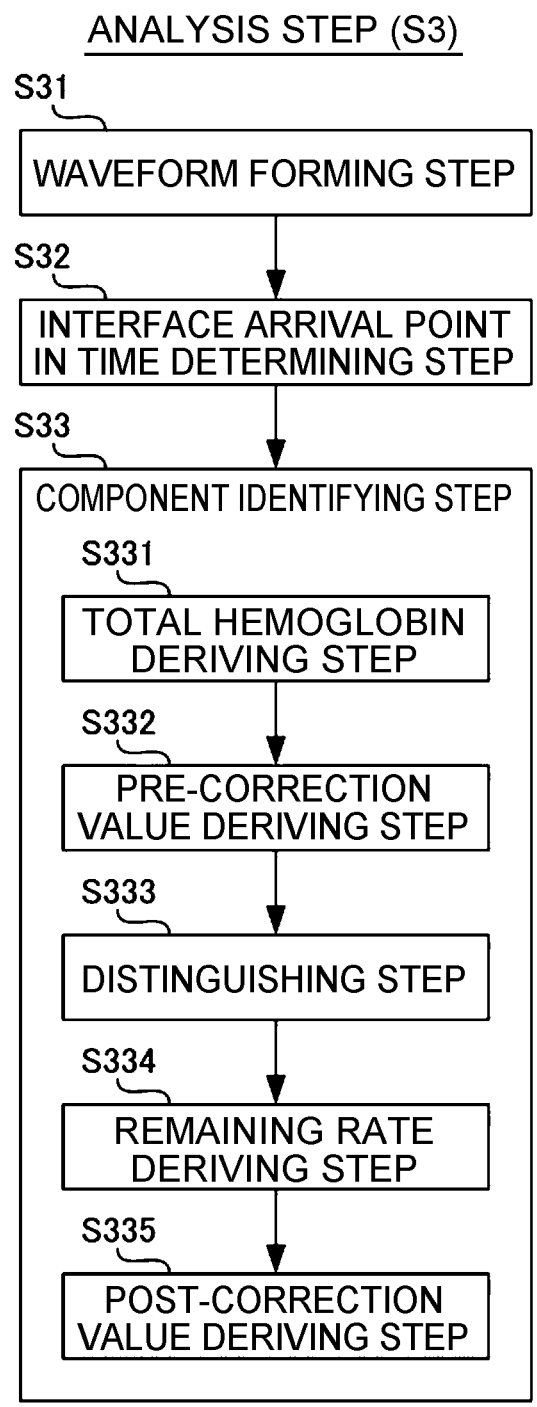
FIG. 11B is a flowchart showing a modified example of processes of the analysis step.
Figure 11C:
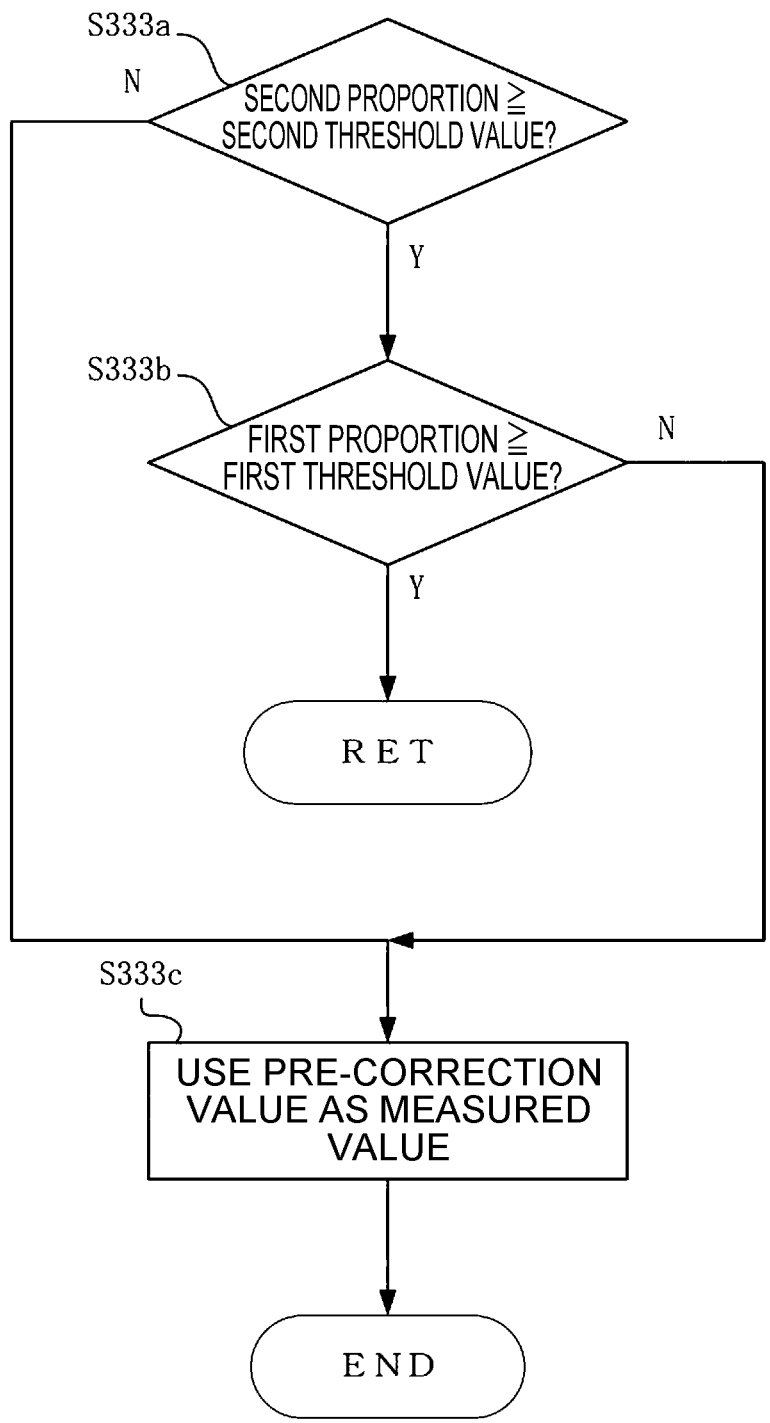
FIG. 11C is a flowchart showing processes of a distinguishing step.

Note that, as shown in FIG. 11B that is another example of the present embodiment, next to the pre-correction value deriving step of S332, in a distinguishing step shown in S333, it may be distinguished whether or not to carry out correction of the pre-correction value (X) that was derived as described above. Namely, in step S333a of FIG. 11C, it is judged whether or not a second proportion is greater than or equal to a second threshold value. Specifically, it is distinguished whether or not the proportion of the peak area of fraction γ, which is in the vicinity of a migration time of 19 seconds and is the fraction adjacent at a side of the earlier time, i.e., at a side at which the positive charge amount is smaller, to the fraction of stable A1c, with respect to either the peak area of the fraction including HbA0 or the entire peak area of the time distribution of the hemoglobin, is greater than or equal to the second threshold value. If it is judged that the second proportion is greater than or equal to the second threshold value, processing moves on to the step shown by S333b. On the other hand, if it is judged that the second proportion is less than the second threshold value, processing moves on to the step shown by S333c, and the pre-correction value (X) is used as the measured value of the fraction of stable A1c, and the analysis step S3 ends.

In step S333b of the distinguishing step shown in S333, it is judged whether or not the first proportion is greater than or equal to the first threshold value. Specifically, it is distinguished whether or not the proportion of the peak area of fraction δ, which is in the vicinity of a migration time of 25 seconds and is the fraction adjacent at a side of the earlier time, i.e., at a side at which the positive charge amount is smaller, to the HbA0 fraction, with respect to either the peak area of the fraction including HbA0 or the entire peak area of the time distribution of the hemoglobin, is greater than or equal to the first threshold value. If it is judged that the first proportion is greater than or equal to the first threshold value, processing returns to FIG. 11A again, and moves on to the step shown by S334. On the other hand, if it is judged that the first proportion is less than the first threshold value, processing moves on to the step shown by S333c, and the pre-correction value (X) is used as the measured value of the fraction of stable A1c, and the analysis step S3 ends.

<Other Points>

It is thought that the charge amounts of the molecular surfaces are close to each other in carbamylated HbA0 and aldehydated HbA0. There are cases in which, in fraction γ, a combined peak of carbamylated HbA0 and aldehydated HbA0 arises. In this case, the peak area of fraction γ that is the combined peak may be used as the peak area of chemically-modified HbA0, and the remaining rate (Q) may be derived from the peak area of fraction γ that is the combined peak. The peak area of the fraction including chemically-modified HbA0 used in correcting the pre-correction value (X) may be used. Similarly, in a substance also generated at the time when HbA0 is carbamylated, and a substance also generated at the time when HBA0 is aldehydated, it is thought that the charge amounts of the molecular surfaces thereof are close to each other, and there are cases in which a combined peak arises in fraction δ. Similarly in this case, the peak area of the chemically-modified HbA0 may be derived from the peak area of the fraction δ that is a combined peak, and the remaining rate (Q) may be derived from the derived peak area of the chemically-modified HbA0.

Further, it is thought that, in carbamylated HbA0 and aldehydated HbA0 that appear in fraction γ, the charge amounts of the molecular surfaces thereof are close to that of labile A1c. Therefore, in the measuring method of the above-described embodiment based on the principles of cation exchange, there are cases in which the peak of the labile A1c forms a combined peak with the respective peaks of carbamylated HbA0 and aldehydated HbA0 that appear in fraction γ, or forms yet another combined peak with the combined peak of carbamylated HbA0 and aldehydated HbA0. In this case, the remaining rate (Q) may be derived by using a revised value obtained by deducting, from the peak area of the combined peak, the peak area of the fraction including the average labile A1c expressed by samples of healthy individuals that have not been chemically modified, and the pre-correction value (X) may be corrected. Otherwise, an accurate amount of labile A1c may be measured by another means, and the remaining rate (Q) may be derived by using the revised amount obtained by deducting the peak area that corresponds to the amount, and the pre-correction value (X) may be corrected.

Further, it is thought that the charge amounts of the molecular surfaces of a substance, which is generated together with carbamylated HbA0 at the time when the HbA0 that appears in fraction δ is carbamylated, and a substance generated together with aldehydated HbA0 at the time when HbA0 is aldehydated, are close to that of the hemoglobin presumed to be HbA1e whose fraction appears in the migration time of fraction δ. Therefore, in the measuring method of the above-described embodiment based on the principles of cation exchange, there are cases in which the peak of the hemoglobin presumed to be HbA1e forms a combined peak with at least one of the substance generated together with carbamylated HbA0 that appears in fraction δ or the substance generated together with aldehydated HbA0.

In this case, the remaining rate (Q) may be derived by using a revised value obtained by deducting, from the peak area of the combined peak, a predetermined peak area value that is the peak area of the fraction including the hemoglobin presumed to be HbA1e expressed by the sample of a healthy individual that is not chemically modified, and the pre-correction value (X) may be corrected. For the peak area of the fraction including hemoglobin assumed to be HbA1e expressed by the sample of a healthy individual that is not chemically modified, samples of plural healthy individuals may be measured, and an average value of the obtained peak areas of the fraction including the hemoglobin presumed to be HbA1e may be used. Otherwise, an amount presumed to be HbA1e may be measured by another means, and the pre-correction value (X) may be corrected by using a revised amount obtained by deducting the peak area that corresponds to that amount.

Example 1

<Effects of Carbamylation>

As Example 1, the method of measuring stable A1c of the present disclosure was shown to be effective in samples in which sodium cyanate was artificially added to a normal sample and the hemoglobin was carbamylated.

[Preparation of Carbamylated Sample]

Whole blood collected from a healthy individual was used as the normal sample. Each of Sample 1 to Sample 4, which was prepared from the normal sample added with sodium cyanate at a final concentration shown in following Table 1 and incubated at 37° C., was used as the above-described specimen Sa (see FIG. 7). The hemoglobin within the sample was carbamylated in accordance with the concentration of the sodium cyanate within the sample.

TABLE 1

| sample | sodium cyanate concentration (mg/dL) |
|---|---|
| 1 | 0 |
| 2 | 12.5 |
| 3 | 18.8 |
| 4 | 25 |

Note that the concentration of sodium cyanate in Sample 1 shown in above Table 1 was 0 mg/dL, which means that the sample was the normal sample as is without being added with sodium cyanate.

[Migration Liquid]

The above-described migration liquid Lm (see FIG. 9) had a following composition.

Citric acid: 40 mM
Sodium chondroitin sulfate C: 1.25% w/v
Piperazine: 20 mM
Polyoxyalkylene alkyl ether (trade name: Emulgen LS-110, manufactured by Kao): 0.1% w/v
Sodium azide: 0.02% w/v
Pro-Clin 300: 0.025% w/v In addition to the above components, dimethyl amino ethanol for pH adjustment was dropped so that the pH of the migration liquid Lm was prepared to 5.0.

[Dilution Liquid]

The above-described dilution liquid Ld (see FIG. 8) had the following composition.

Citric acid: 38 mM
Sodium chondroitin sulfate C: 0.95% w/v
1-(3-Sulfopropyl)pyridinium hydroxide inner salt (NDSB-201): 475 mM 2-Morpholinoethanesulfonic acid (MES): 19 mM
Polyoxyalkylene alkyl ether (trade name: Emulgen LS-110, manufactured by Kao): 0.4% w/v
Sodium azide: 0.02% w/v
ProClin 300: 0.025% w/v In addition to the above components, dimethyl amino ethanol for pH adjustment was dropped so that the pH of the dilution liquid Ld was prepared to 6.0.

[Mixed Specimen Sm]

One point five μL of the specimen Sa was added to 60 μL of the dilution liquid Ld, and the mixed specimen Sm (see FIG. 8 to FIG. 10) was prepared. The mixed specimen Sm was provided to the above-described analyzing system A1, and separation analysis of hemoglobin was carried out.

[Electropherogram]

Figure 15:
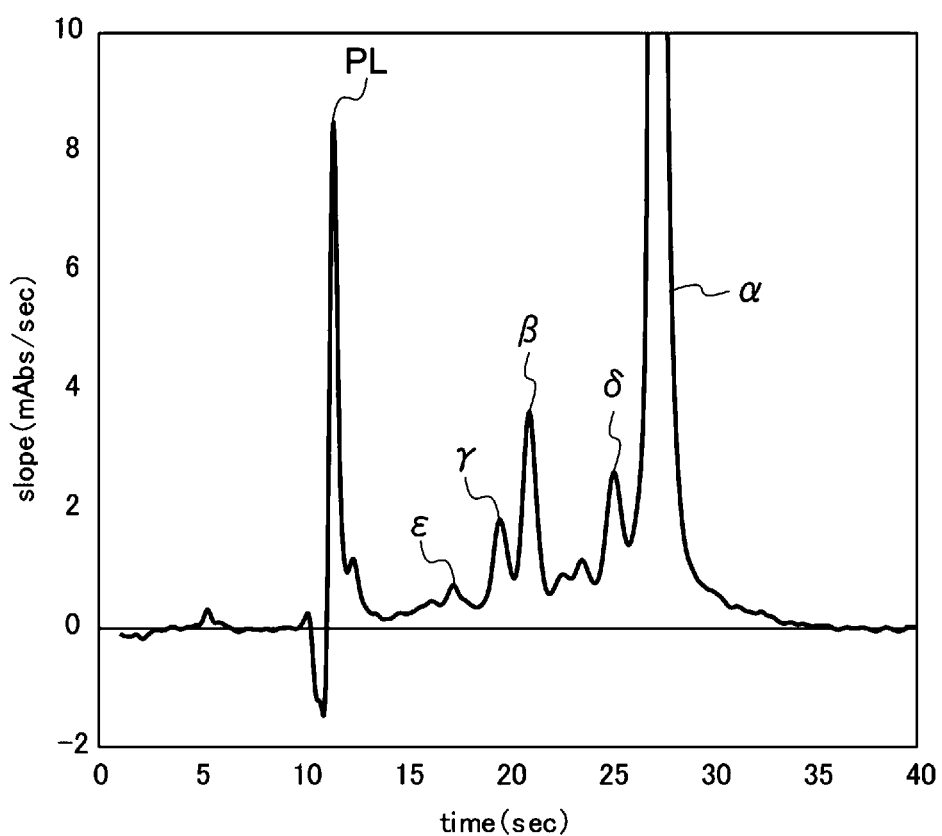
FIG. 15 shows the electropherogram of Sample 1 in Example 1.

An electropherogram was obtained with a point in time at which a voltage was applied being a point in time of start of the separation analysis, and the point in time at which the voltage was applied being a point in time of 0 seconds. The electropherogram of Sample 1 to which sodium cyanate was not added is shown in FIG. 15. The interface arrival point in time at which the furthest point PL was detected was in a vicinity of a migration time of 11.5 seconds. Further, fraction E that was an HbF fraction had a peak in the vicinity of a migration time of 17.3 seconds. Fraction β that was a stable A1c fraction had a peak in the vicinity of a migration time of 21 seconds. Fraction α that was an HbA0 fraction had a peak in the vicinity of a migration time of 27.3 seconds. Further, fraction γ, which had a peak in the vicinity (19.4 seconds) of a migration time of 19 seconds which was earlier than fraction β, was a fraction including labile A1c, and also including HbA0 subjected to carbamylation. Further, fraction δ, which had a peak in the vicinity (25.2 seconds) of a migration time of 25 seconds which was earlier than fraction a, included a substance that was generated together with carbamylated HbA0 at the time when HbA0 was carbamylated.

Figure 16:
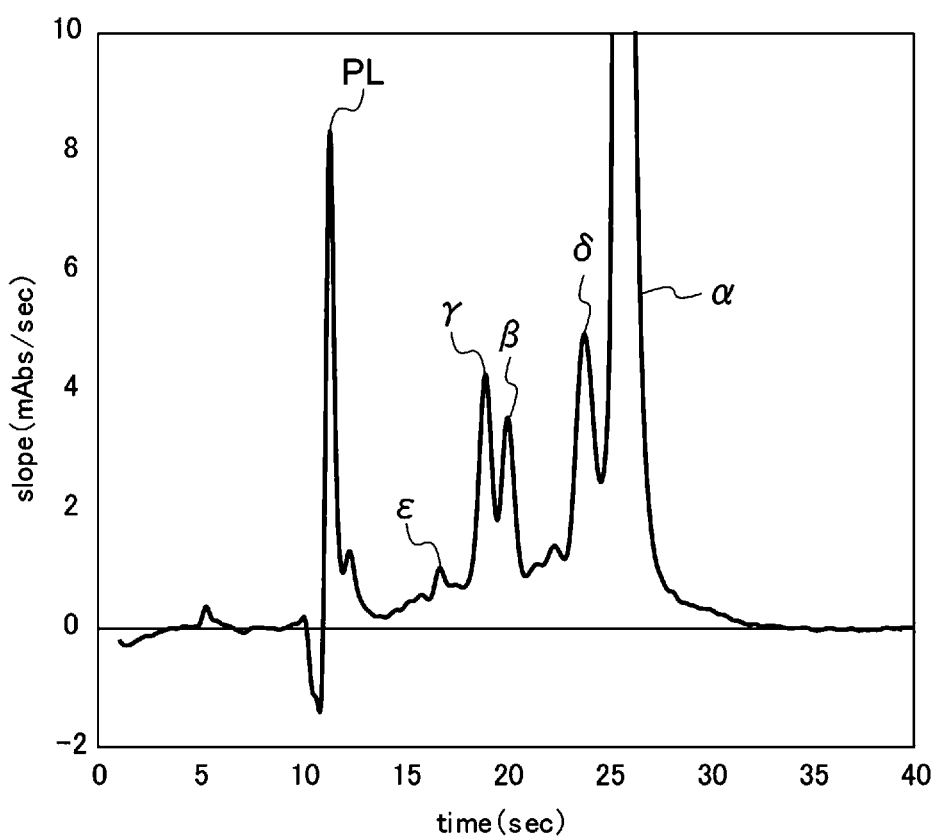
FIG. 16 shows the electropherogram of Sample 2 in Example 1.

The electropherogram of Sample 2, in which sodium cyanate was added in a concentration of 12.5 mg/dL, was as shown in FIG. 16. The interface arrival point in time when the furthest point PL was detected was almost the same as Sample 1, and the peaks of fraction ε, fraction γ, fraction β, fraction δ and fraction α were observed at migration times of 16.7 seconds, 19.0 seconds, 20.0 seconds, 23.8 seconds and 25.6 seconds, respectively. Further, the areas of fraction γ and fraction δ were greater than in Sample 1.

Figure 17:
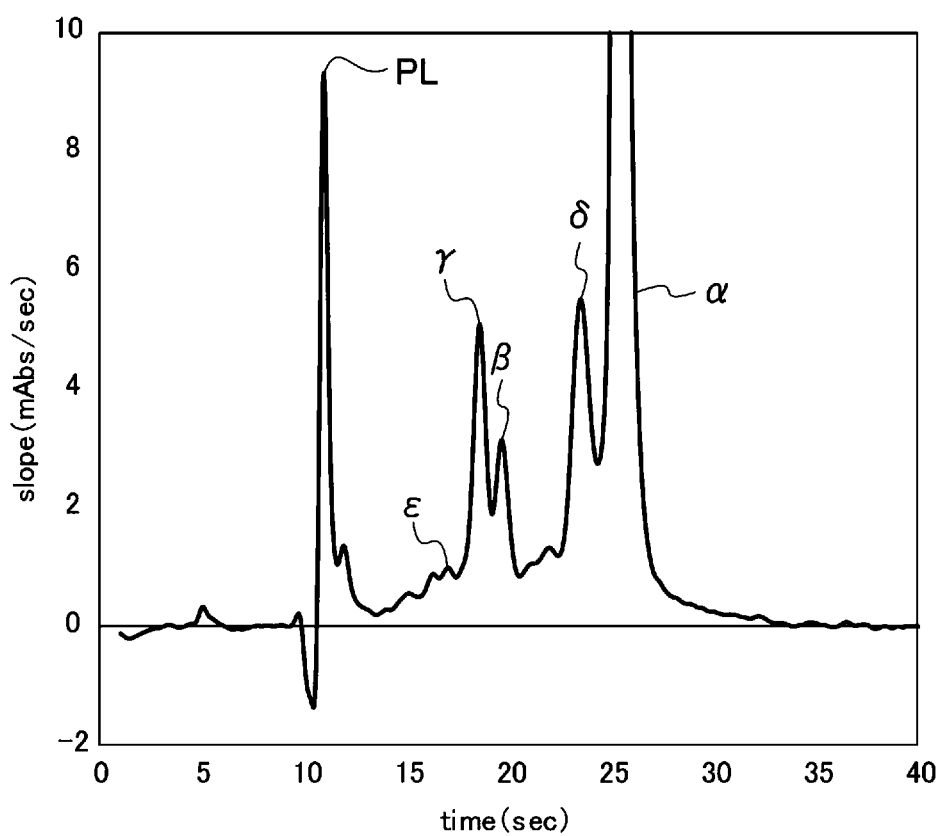
FIG. 17 shows the electropherogram of Sample 3 in Example 1.

The electropherogram of Sample 3, in which sodium cyanate was added in a concentration of 18.8 mg/dL, was as shown in FIG. 17. The interface arrival point in time when the furthest point PL was detected was almost the same as Sample 1 and Sample 2, and the peaks of fraction ε, fraction γ, fraction β, fraction δ and fraction α were observed at migration times of 16.9 seconds, 18.5 seconds, 19.6 seconds, 23.5 seconds and 25.4 seconds, respectively, which were substantially the same times as in Sample 2. Further, the areas of fraction γ and fraction δ were further greater than in Sample 2.

Figure 18:
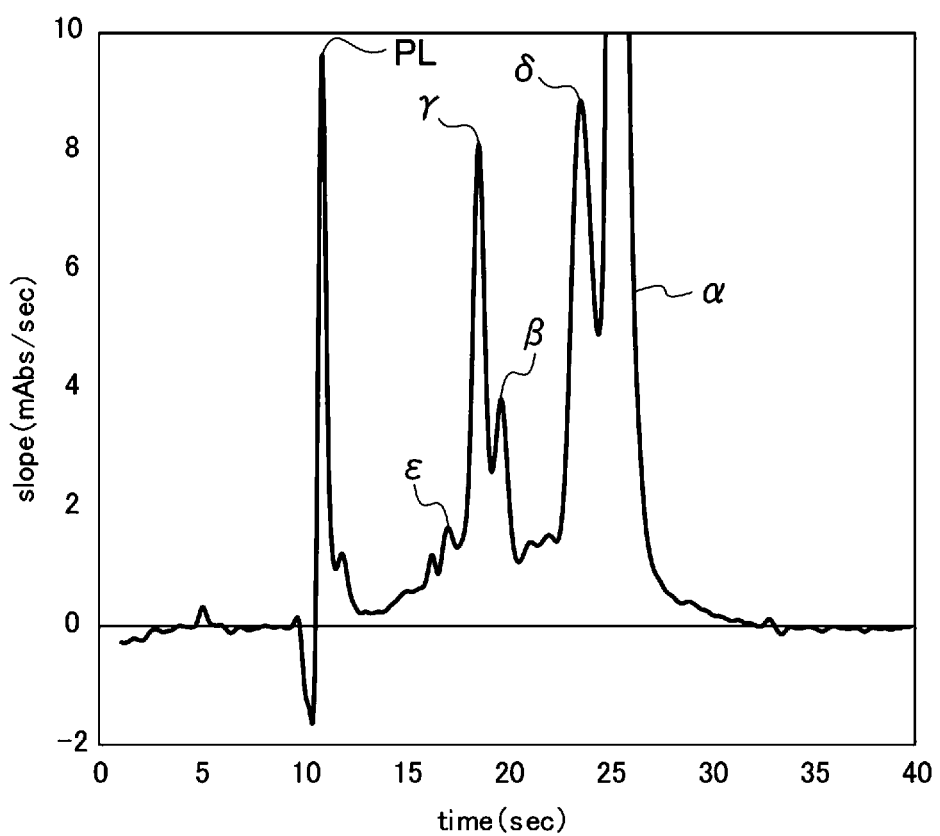
FIG. 18 shows the electropherogram of Sample 4 in Example 1.

The electropherogram of Sample 4, in which sodium cyanate was added in a concentration of 25 mg/dL, is shown in FIG. 18. The interface arrival point in time when the furthest point PL was detected is almost the same as Sample 1 to Sample 3, and the migration times at which the peaks of fraction ε, fraction γ, fraction β, fraction δ and fraction α were observed also were substantially the same as Sample 3. However, the areas of fraction γ and fraction δ were further greater than in Sample 3. Note that the times at which the respective fractions were observed in Sample 1, Sample 2, Sample 3 and Sample 4 differed in accordance with the sample, but did not affect the measurement of stable A1c in the present Example.

[Derivation of Pre-Correction Value (X)]

From fraction β in FIG. 15 to FIG. 18, pre-correction values (X), which was the proportion of the peak area of stable A1c, were derived as shown in following Table 2.

TABLE 2

| sample | pre-correction value (X) (%) | relative error (%) |
|---|---|---|
| 1 | 6.48 | 0.0 |
| 2 | 6.28 | −3.1 |
| 3 | 6.26 | −3.3 |
| 4 | 6.06 | −6.5 |

In deriving the pre-correction values (X) in above Table 2, first, the total sum of the area of the portions where the slope values were greater than or equal to 0 in each electropherogram (except for the portion where PL was the peak) was derived, and this was made to be the entire peak area of the fractions including hemoglobin. The entire peak area of the fractions including hemoglobin included the peak area (A) of HbA0 identified as fraction α. Then, the pre-correction values (X) in above Table 2 were derived from the proportion of the peak area of fraction β with respect to the entire peak area of the fraction including hemoglobin.

As shown in above Table 2, it was confirmed that the pre-correction value (X) became lower in accordance with increase of the concentration of sodium cyanate in the sample. Further, the value of the relative error, which expressed the proportion of the increase or decrease with respect to pre-correction value (X) of Sample 1 (i.e., the proportion of the value obtained by subtracting 6.48%, which was the pre-correction value (X) of Sample 1, from the pre-correction value (X) of the sample, with respect to the pre-correction value (X) of Sample 1), also became larger in accordance with the increase of the concentration of the sodium cyanate. This shows that the stable A1C amount decreased by being subjected to carbamylation by sodium cyanate.

[Correction in Accordance with Fraction γ]

Next, correction of the pre-correction value (X) was carried out as shown in following Table 3 by using fraction γ that is adjacent, at a side at which the positive charge amount was smaller, i.e., the side at which the migration speed was faster, to fraction β identified as stable A1c.

TABLE 3

| sample | fraction γ (%) | modification rate (P) (%) | remaining rate (Q) (%) | post-correction value (Y) (%) | relative error (%) |
|---|---|---|---|---|---|
| 1 | 2.9 | — | — | 6.48 | 0.0 |
| 2 | 6.1 | 3.1 | 96.9 | 6.48 | 0.0 |
| 3 | 8.1 | 5.1 | 94.9 | 6.60 | 1.8 |
| 4 | 9.6 | 6.6 | 93.4 | 6.49 | 0.1 |

The proportion of the area of fraction γ with respect to the entire peak area of the fractions including hemoglobin was as shown in the left end column in above Table 3. Specifically, these proportions were 2.9% in Sample 1, 6.1% in Sample 2, 8.1% in Sample 3, and 9.6% in Sample 4.

It is known that labile A1c (L-A1c) is included in fraction γ. Thus, 3%, which was thought to be the constant proportion of the peak area derived from labile A1c, was used as the predetermined peak area, and was deducted from the above-described proportion of the peak area of fraction γ, and the modification rate (P) shown in above Table 3 was thereby derived. Note that the proportion of the peak area derived from labile A1c may be a statistical value of the proportion of the peak area of the fraction including labile A1c (L-A1c) obtained by separating and analyzing samples of plural healthy individuals that are thought to have not been subjected to effects of carbamylation and aldehydation, and is not limited to the aforementioned 3%. Here, fraction γ in Sample 1 was 2.9% and was less than this 3%, and this case was treated as the modification rate (P) being 0 in terms of computation. Table 3 shows that the modification rate (P) increased in accordance with the increase of the concentration of sodium cyanate within the sample. Note that the modification rate (P) was the proportion of the peak area including carbamylated HbA0 with respect to the entire peak area of the fractions including hemoglobin. The entire peak area of the fractions including hemoglobin approximates the total value of the peak area of the fraction including HbA0 and the peak area of the fraction including the carbamylated HbA0. Therefore, appropriate correction can be performed in this way by using the modification rate (P) that is the proportion of the peak area including carbamylated HbA0, with respect to the entire area of the fractions including hemoglobin.

The value obtained by subtracting the modification rate (P) from 1 was the remaining rate (Q, expressed as a percentage) in above Table 3. It was thought that the stable A1c that remained at the proportion of the remaining rate (Q) was the pre-correction value (X) in above Table 2, i.e., fraction β appearing in the electropherogram. Accordingly, the post-correction value (Y) in above Table 3, which was the value obtained by dividing the pre-correction value (X) by the remaining rate (Q), was thought to be the proportion of the total value of the peak area of the fraction including stable A1c that remained without having been chemically modified, and the peak area of the fraction including chemically-modified stable A1c, with respect to the entire peak area of the fractions including hemoglobin. Here, from above Table 2, while the absolute value of the relative error based on the pre-correction value (X) was a maximum of 6.5% in Sample 4, from above Table 3, the absolute value of the relative error based on the post-correction value (Y) (i.e., the proportion, with respect to the pre-correction value (X) of Sample 1, of the value obtained by subtracting the pre-correction value (X) of Sample 1 (see FIG. 2), which was thought to not have been affected by chemical modification, from the post-correction value (Y) of the sample) was a maximum of 1.8% in Sample 3. Therefore, by carrying out the correction, the range of relative errors that arose due to chemical modification was narrowed.

Accordingly, it can be thought that, due to correction using fraction γ, effects of chemical modification due to carbamylation are reduced or eliminated, and a value nearer to the proportion of stable A1c that reflects the average blood sugar level of previous one to two months is determined.

[Correction in accordance with Fraction δ]

In the correction in accordance with fraction δ, 4%, which was a proportion of the peak area of fraction δ that was usually had by a sample of a healthy individual thought to not have been subjected to carbamylation or aldehydation, was deducted, as a predetermined peak area, from the proportion of the peak area of fraction δ with respect to the entire peak area of the fractions including hemoglobin listed in the left end column in following Table 4. Note that the deducted value may be a statistical value of the proportion of the peak areas of fraction δ obtained by separating and analyzing samples of plural healthy individuals, and is not necessarily limited to this 4%. Further, the peak area of a substance also generated at the time when HbA0 was chemically modified was about 1.65 times of fraction γ that was the peak area of the carbamylated HbA0. From this, the value, which was obtained by dividing the value obtained by deducting 4% from fraction δ, by 1.65 that is a predetermined factor (a) was considered to be the proportion of the peak area of carbamylated HbA0 with respect to the entire peak area of the fractions including hemoglobin, and this was used as the modification rate (P). In addition, the deriving of the remaining rates (Q), the post-correction values (Y) and the relative errors were the same as in Table 3. However, the post-correction values (Y) in Table 4 were values obtained by dividing the pre-correction values (X) in above Table 2 by the remaining rates (Q) of Table 4. Further, in the same way as in Table 3, the relative error in Table 4 was the proportion, with respect to the pre-correction value (X) of Sample 1, of the value obtained by subtracting the pre-correction value (X) of Sample 1 (see Table 2) that was thought to not have been affected by chemical modification, from the post-correction value (Y) of the sample.

TABLE 4

| sample | fraction δ (%) | fraction δ-4 (%) | modification rate (P) (%) | remaining rate (Q) (%) | post-correction value (Y) (%) | relative error (%) |
|---|---|---|---|---|---|---|
| 1 | 4.5 | 0.5 | 0.3 | 99.7 | 6.50 | 0.3 |
| 2 | 9.3 | 5.3 | 3.2 | 96.8 | 6.49 | 0.1 |
| 3 | 11.8 | 7.8 | 4.7 | 95.3 | 6.57 | 1.5 |
| 4 | 16.1 | 12.1 | 7.3 | 92.7 | 6.54 | 0.9 |

From Table 4 as well, it can be said that the range of the relative errors of the post-correction value (Y) was smaller than the range of the relative errors (see Table 2) of the pre-correction value (X) before correction. Accordingly, it can be thought that, due to correction using fraction δ, effects of chemical modification due to carbamylation are reduced or eliminated, and a value nearer to the proportion of stable A1c that reflects the average blood sugar level of previous one to two months is determined.

[Summary of Effects of Carbamylation]

As a summary of above Table 2 to Table 4, the relative errors in a case in which correction was not carried out, in a case in which correction was carried out in accordance with fraction γ, and in a case in which correction was carried out in accordance with fraction δ, with respect to the sodium cyanate concentration of each sample, are shown in following Table 5.

TABLE 5

| sample | sodium cyanate concentration (mg/dL) | relative error (%) | | |
|---|---|---|---|---|
| | | no correction | correction using fraction γ | correction using fraction δ |
| 1 | 0 | 0.0 | 0.0 | 0.3 |
| 2 | 12.5 | −3.1 | 0.0 | 0.1 |
| 3 | 18.8 | −3.3 | 1.8 | 1.5 |
| 4 | 25 | −6.5 | 0.2 | 0.9 |

Figure 19:
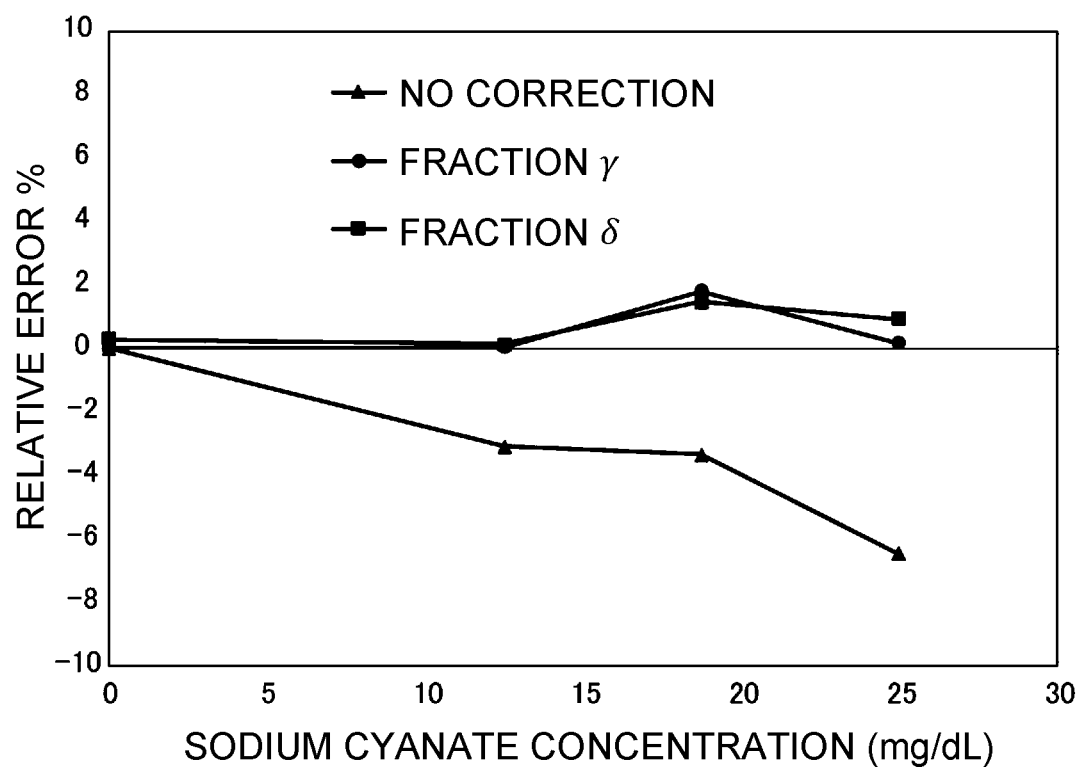
FIG. 19 is a graph showing results of correcting the stable A1c amount in Example 1.

As clearly shown also by FIG. 19 in which the results of above Table 5 were graphed, it was confirmed that effects of carbamylation on stable A1c due to sodium cyanate were at least reduced by both of the methods of correction.

[First Proportion and Second Proportion]

Note that a case in which it was distinguished whether or not the above-described correction in accordance with fraction γ or fraction δ was to be carried out by using the first proportion and the second proportion, on the pre-correction values (X) shown in above Table 2, is described hereinafter.

The second proportion that was a proportion of fraction γ that was adjacent, at a side at which the positive charge amount was smaller, i.e., the side at which the migration speed was faster, to fraction β identified as stable A1c, with respect to the entire peak area of the fractions including hemoglobin, was as shown in following Table 6. Further, the first proportion, which was derived from fraction δ that was adjacent, at a side at which the positive charge amount was smaller, i.e., the side at which the migration speed was faster, to fraction α identified as HbA0, with respect to the entire peak area including hemoglobin, also was shown in following Table 6.

TABLE 6

| sample | first proportion (fraction δ) (%) | second proportion (fraction γ) (%) |
|---|---|---|
| 1 | 4.5 | 2.9 |
| 2 | 9.3 | 6.1 |
| 3 | 11.8 | 8.1 |
| 4 | 16.1 | 9.6 |

Namely, the second proportions, each of which was the proportion of the area of fraction γ with respect to the entire peak area of the fractions including hemoglobin, were 2.9% in Sample 1, 6.1% in Sample 2, 8.1% in Sample 3, and 9.6% in Sample 4. Further, the first proportions, each of which was the proportion of the area of fraction δ, were 4.5% in Sample 1, 9.3% in Sample 2, 11.8% in Sample 3, and 16.1% in Sample 4.

[Judgement on Necessity of Correction]

It was judged whether or not the first proportion in above Table 6 was greater than or equal to the first threshold value. As an example, the first threshold value was 9% which was a value exceeding the maximum value of the peak area of fraction δ usually observed in a sample that was thought to have not been subjected to effects of carbamylation and aldehydation. Similarly, it was judged whether or not the second proportion was greater than or equal to the second threshold value. As an example, the second threshold value was 5% which was a value exceeding the maximum value of the peak area of fraction γ usually observed, by the migration speed, in a sample that was thought to have a usual amount of labile A1c without having been carbamylated or aldehydated, i.e., the sample of a healthy individual.

First, for Samples 2 to 4, the first proportion in each case was greater than or equal to 9% which is the first threshold value. Further, the second proportion as well was greater than or equal to 5% which is the second threshold value. Therefore, it was judged that the proportion of the peak area of the fraction including stable A1c, with respect to either the peak area of the fraction including HbA0 or the entire peak area of the electropherogram, was to be corrected by the remaining rate. On the other hand, for Sample 1, the second proportion was less than 5% that is the second threshold value, and further, the first proportion was less than 9% that is the first threshold value. Therefore, it was judged that the aforementioned correction was not to be carried out. Note that, in the present Example, it was judged whether the first proportion was greater than or equal to the first threshold value, and the second proportion was greater than or equal to the second threshold value. However, whether or not to carry out correction may be judged by judging only whether the first proportion is greater than or equal to the first threshold value.

[Correction in Accordance with Fraction γ]

Next, correction of the pre-correction values (X) of above Table 2 was carried out as shown in following Table 7 by using fraction γ that was adjacent, at a side at which the positive charge amount was smaller, i.e., the side at which the migration speed was faster, to fraction β identified as stable A1c.

TABLE 7

| sample | fraction γ (%) | modification rate (P) (%) | remaining rate (Q) (%) | post-correction value (Y) (%) | relative error (%) |
|---|---|---|---|---|---|
| 1 | 2.9 | — | — | 6.48 | 0.0 |
| 2 | 6.1 | 3.1 | 96.9 | 6.48 | 0.0 |
| 3 | 8.1 | 5.1 | 94.9 | 6.60 | 1.8 |
| 4 | 9.6 | 6.6 | 93.4 | 6.49 | 0.1 |

The proportion of the area of fraction γ with respect to the peak area of the fractions including hemoglobin was as shown in the left end column in above Table 7. Specifically, the proportions were 2.9% in Sample 1, 6.1% in Sample 2, 8.1% in Sample 3, and 9.6% in Sample 4.

In Sample 1, as shown in Table 6, the first proportion was less than the first threshold value, and further, the second proportion was less than the second threshold value. Accordingly, the pre-correction value (X) shown in Table 2 was used as the measured value of the stable A1c fraction, without being corrected by the remaining rate (Q). Note that, for convenience of comparison with the post-correction values (Y) and the relative errors of Sample 2 to Sample 4, 6.48% that was the pre-correction value (X) was shown in the post-correction value (Y) column in Table 7.

On the other hand, as shown in Table 6, in Samples 2 to 4, the first proportion was greater than or equal to the first threshold value, and the second proportion was greater than or equal to the second threshold value. Thus, first, as the peak area of fraction γ that was usually had by a sample of a healthy individual that was thought to have a usual amount of labile A1c and was not subjected to effects of carbamylation and aldehydation, 3%, which was the average value of the peak areas of fraction γ of plural healthy individuals, was used as the predetermined peak area, and was deducted from the peak area of fraction γ. The value was the modification rate (P) in above Table 7. The value obtained by subtracting the value from 1 was the remaining rate (Q, expressed as a percentage) in above Table 7, and it was thought that the stable A1c that remained in the proportion is the pre-correction value (X) in above Table 2, i.e., appeared in the electropherogram as fraction β. Accordingly, it was thought that post-correction value (Y) in above Table 7, which was the value obtained by dividing the pre-correction value (X) by the remaining rate (Q), was the actual stable A1c amount, and the post-correction value (Y) was used as the measured value of the stable A1c fraction. Here, from above Table 2, when the absolute value of the relative error based on the pre-correction value (X) was a maximum of 6.5% in Sample 4, from above Table 7, the absolute value of the relative error based on the post-correction value (Y) (i.e., the relative error is the proportion, with respect to the pre-correction value (X) of Sample 1, of the value obtained by subtracting the pre-correction value (X) (see Table 2) of Sample 1, which was thought to have not been affected by chemical modification, from the post-correction value (Y) of the sample) was a maximum of 1.8% in Sample 3. Therefore, by judging the necessity of correction, and carrying out correction in cases in which it was judged that correction was needed, the range of the relative errors that arose due to chemical modification was small.

Accordingly, it can be thought that, by judging that necessity of correction, and carrying out correction by using fraction γ in a case in which it is judged that correction is needed, effects of chemical modification due to carbamylation are reduced or eliminated, and a value nearer to the proportion of stable A1c that reflects the average blood sugar level of previous one to two months is determined.

[Correction in Accordance with Fraction δ]

Next, correction of the pre-correction values (X) of above Table 2 was carried out as shown in following Table 8 by using fraction δ that was adjacent, at a side at which the positive charge amount was smaller, i.e., the side at which the migration speed was faster, to fraction α identified as HbA0.

TABLE 8

| sample | fraction δ (%) | fraction δ-4 (%) | modification rate (P) (%) | remaining rate (Q) (%) | post-correction value (Y) (%) | relative error (%) |
|---|---|---|---|---|---|---|
| 1 | 4.5 | — | — | — | 6.48 | 0.0 |
| 2 | 9.3 | 5.3 | 3.2 | 96.8 | 6.49 | 0.1 |
| 3 | 11.8 | 7.8 | 4.7 | 95.3 | 6.57 | 1.5 |
| 4 | 16.1 | 12.1 | 7.3 | 92.7 | 6.54 | 0.9 |

The proportion of the area of fraction δ with respect to the entire peak area of the fractions including hemoglobin was as shown in the left end column in above Table 8. Specifically, the proportions were 4.5% in Sample 1, 9.3% in Sample 2, 11.8% in Sample 3, and 16.1% in Sample 4.

Here, as described above, in Sample 1, as shown in Table 6, the first proportion was less than the first threshold value, and further, the second proportion was less than the second threshold value. Accordingly, correction by the remaining rate (Q) was not carried out. Although the pre-correction value (X) of Sample 1 was not corrected, the pre-correction value (X) of 6.48% was shown in the post-correction value (Y) column in Table 8 for convenience of comparison with the post-correction values (Y) and the relative errors of Sample 2 to Sample 4.

On the other hand, as shown in Table 6, in Samples 2 to 4, the first proportion was greater than or equal to the first threshold value, and the second proportion was greater than or equal to the second threshold value. Thus, first, as the peak area of fraction δ usually observed in a sample of a healthy individual that was thought to not have been subjected to effects of carbamylation and aldehydation, 4%, which was the average value of the peak areas of fraction δ of plural healthy individuals, was used as the predetermined peak area, and was deducted from the peak area of fraction δ. Further, the peak area of a substance, which was also generated at the time when HbA0 was chemically modified, was about 1.65 times fraction γ that was the peak area of carbamylated HbA0. From these, the value, which was obtained by dividing, by a predetermined factor (a) that was this 1.65, the value obtained by deducting 4% as the predetermined peak area value from fraction δ, was considered to be the proportion of the peak area of carbamylated HbA0 with respect to the entire peak area of the fractions including hemoglobin, and was used as the modification rate (P). In addition, derivation of the remaining rate (Q), the post-correction value (Y) and the relative error were the same as in Table 4. However, the post-correction value (Y) in Table 8 was a value obtained by dividing the pre-correction value (X) in above Table 2 by the remaining rate (Q) of Table 8. Further, in the same way as in Table 4, the relative error in Table 8 was the proportion, with respect to the pre-correction value (X) of Sample 1, of the value obtained by subtracting the pre-correction value (X) of Sample 1 (see Table 2), that was thought to not have been affected by chemical modification, from the post-correction value (Y) of the sample.

From Table 8 as well, it can be said that the range of the relative errors of the post-correction value (Y) was smaller than the range of the relative errors (see Table 2) of the pre-correction value (X) before correction. Accordingly, even if a judgment on the necessity of correction is carried out, and, when correction is judged to be necessary, correction is carried out by using fraction δ, it can be thought that effects of chemical modification due to carbamylation are reduced or eliminated, and a value nearer to the proportion of stable A1c that reflects the average blood sugar level of previous one to two months is determined.

[Summary of Effects of Carbamylation]

As a summary of above Table 2, Table 7 and Table 8, following Table 9 lists the relative errors in a case in which measurement was carried out without correcting the samples that were processed by the respective sodium cyanate concentrations, and in a case in which a judgment on the necessity of correction was carried out, and, when it was judged that correction was needed, the sample was measured by using correction in accordance with fraction γ, and in a case in which a judgment on the necessity of correction was carried out, and, when it was judged that correction was needed, the sample was measured by using correction in accordance with fraction δ.

TABLE 9

| sample | sodium cyanate concentration (mg/dL) | relative error (%) no correction | correction using fraction γ | correction using fraction δ |
|---|---|---|---|---|
| 1 | 0 | 0.0 | 0.0 | 0.0 |
| 2 | 12.5 | −3.1 | 0.0 | 0.1 |
| 3 | 18.8 | −3.3 | 1.8 | 1.5 |
| 4 | 25 | −6.5 | 0.2 | 0.9 |

When the relative errors listed in above Table 9 were compared with the relative errors listed in above Table 5, there was no change with respect to correction using fraction γ. However, with regard to correction using fraction δ, the relative error of Sample 1 was 0.3% in Table 5, whereas in Table 9, the relative error became even smaller and was 0.0%. Due to the above, it was confirmed that, after carrying out judgment using the first threshold value and the second threshold value, by correcting the pre-correction value (X) by the remaining rate (Q) if needed, it was possible to eliminate, to the highest degree, the effects of carbamylation of stable A1c by sodium cyanate, without conversely making the relative error larger by unnecessary correction.

Example 2

<Effects of Aldehydation>

As Example 2, the method of measuring stable A1c of the present disclosure was shown to be effective also in samples in which acetaldehyde was artificially added to a normal sample and the hemoglobin was aldehydated.

[Preparation of Aldehydated Sample]

Whole blood collected from a healthy individual was used as the normal sample. Acetaldehyde was added to the normal sample such that the final concentrations shown in following Table 10 were obtained, and Sample 1 to Sample 4 that were incubated at 37° C. were prepared, and each of these was used as the above-described specimen Sa (see FIG. 7). The hemoglobin within the sample was aldehydated in accordance with the concentration of the acetaldehyde within the sample.

TABLE 10

| sample | acetaldehyde concentration (mg/dL) |
| --- | --- |
| 5 | 0 |
| 6 | 12.5 |
| 7 | 25 |

Note that the concentration of acetaldehyde within sample 5 of above Table 10 was 0 mg/dL. This means that acetaldehyde was not added, and the normal sample remained as was. Further, the migration liquid Lm, the dilution liquid Ld, and the mixed specimen Sm were the same as those in above-described Example 1.

[Electropherogram]

Figure 20:
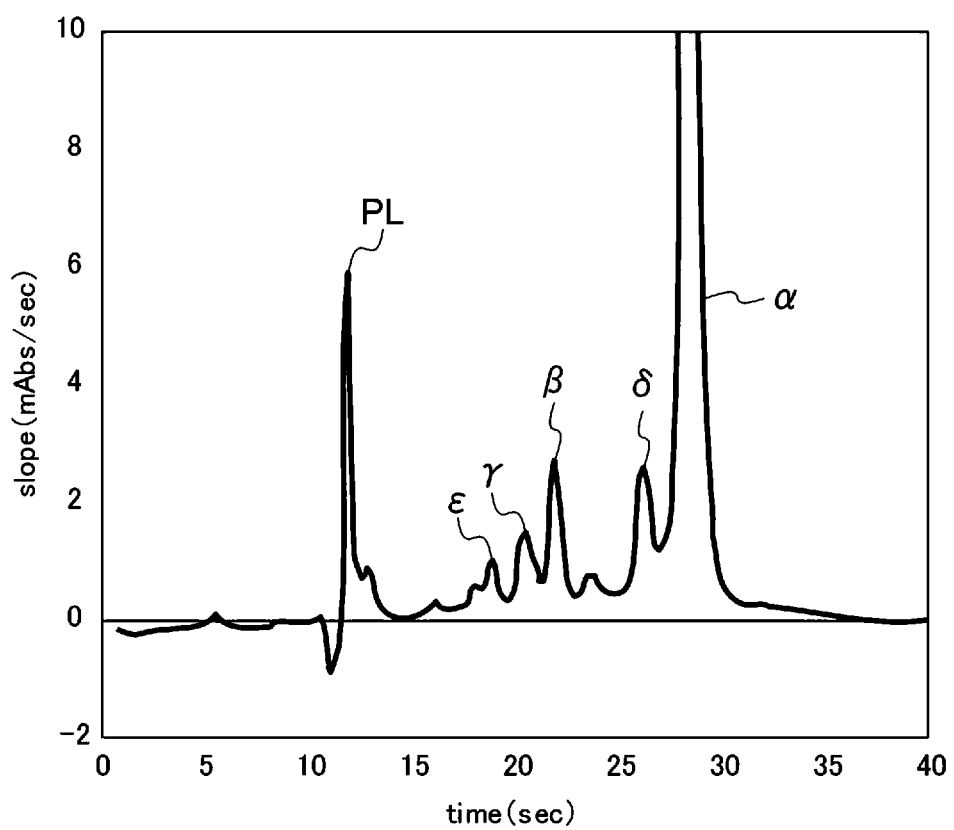
FIG. 20 shows the electropherogram of Sample 5 in Example 2.

An electropherogram was obtained with the point in time at which a voltage was applied being the point in time of the start of the separation analysis, and the point in time at which the voltage was applied being the point in time of 0 seconds. The electropherogram of Sample 5 to which acetaldehyde was not added is shown in FIG. 20. The point in time at which the voltage was applied was the point in time of the start of the separation analysis, and was the point in time at which the migration time was 0 seconds in the electropherogram. The interface arrival point in time at which the furthest point PL was detected is in a vicinity of a migration time of 11.9 seconds. Further, fraction E that was the HbF fraction had a peak in the vicinity of a migration time of 18.8 seconds. Fraction β that was the stable A1c fraction had a peak in the vicinity of a migration time of 21.9 seconds. Fraction α that was the HbA0 fraction had a peak in the vicinity of a migration time of 28.3 seconds. Further, fraction γ, which had a peak in the vicinity of a migration time of 20.4 seconds that was earlier than fraction β, was the fraction including labile A1c, but HbA0 subjected to aldehydation was also included in the fraction. Further, HbA0 that was subjected to aldehydation was included also in fraction δ that had a peak in the vicinity of a migration time of 26.2 seconds which was earlier than fraction a.

Figure 21:
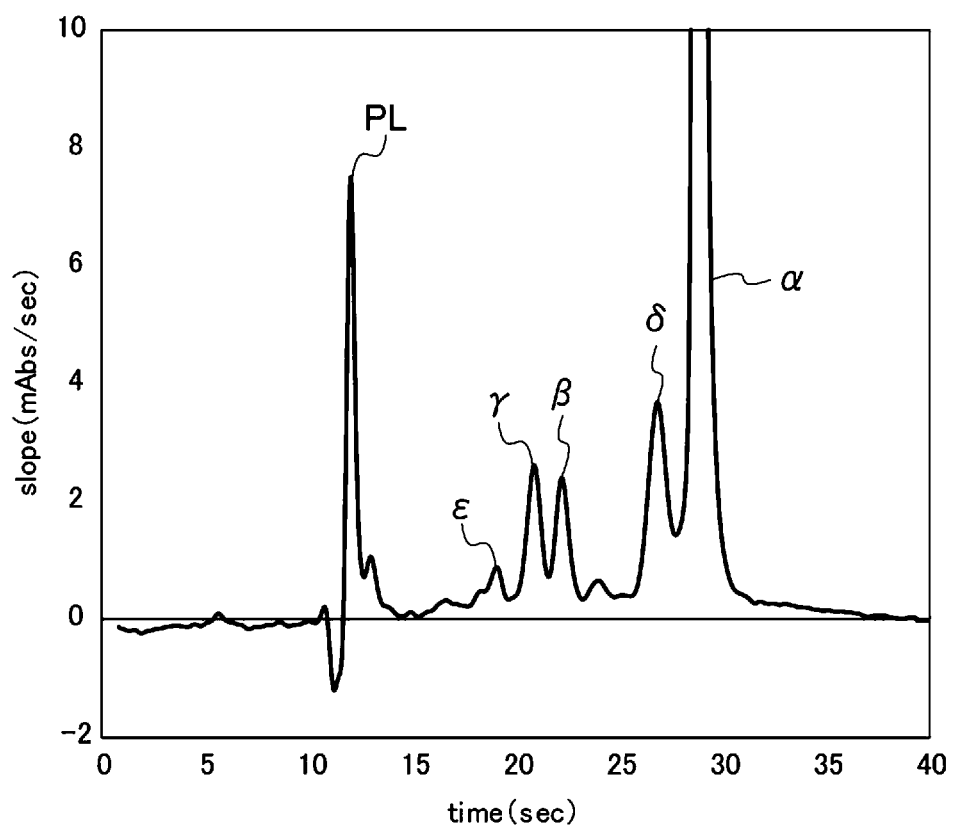
FIG. 21 shows the electropherogram of Sample 6 in Example 2.
Figure 22:
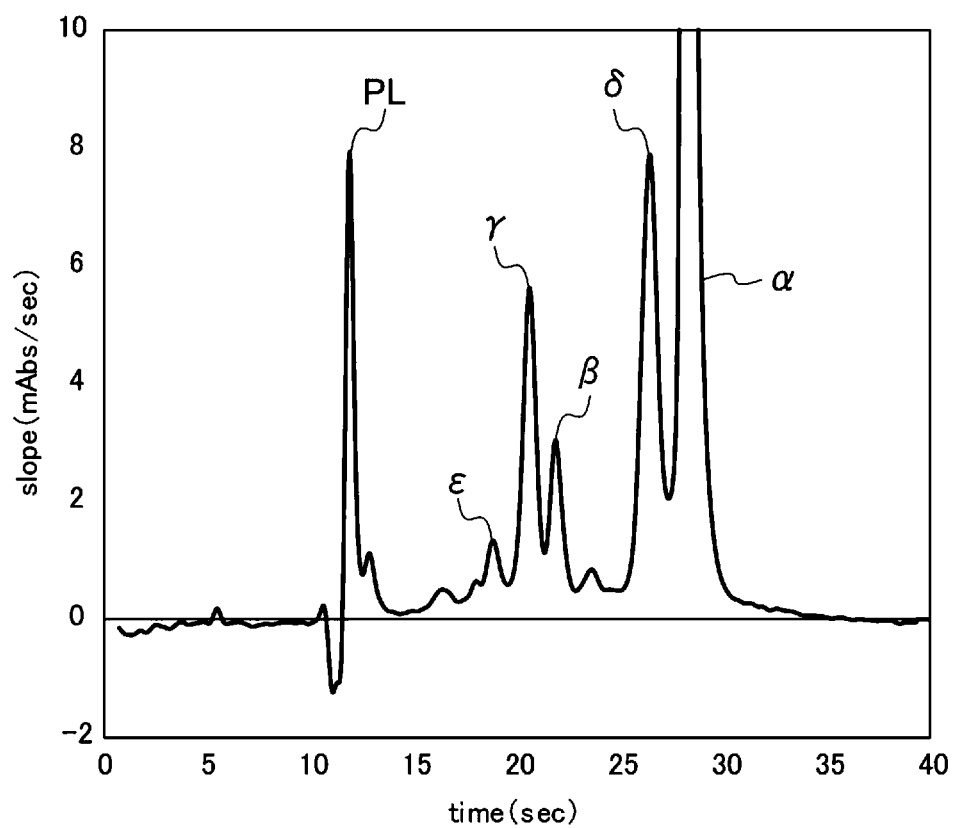
FIG. 22 shows the electropherogram of Sample 7 in Example 2.

The electropherogram of Sample 6, in which acetaldehyde was added in a concentration of 12.5 mg/dL, was as shown in FIG. 21. Further, the electropherogram of Sample 7, in which acetaldehyde was added in a concentration of 25 mg/dL, was as shown in FIG. 22. In the same way as in the above-described case of carbamylation, it was confirmed from FIG. 20 to FIG. 22 that the areas of fraction γ and fraction δ increased as the concentration of the acetaldehyde increases.

[Derivation of Pre-Correction Value (X)]

From fraction β in FIG. 20 to FIG. 22, the pre-correction value (X), which was the proportion of the peak area of stable A1c, was derived as shown in following Table 11. Note that the method of deriving the pre-correction value (X) was the same as in above-described Example 1.

TABLE 11

| sample | pre-correction value (X) (%) | relative error (%) |
| --- | --- | --- |
| 5 | 5.47 | 0.0 |
| 6 | 5.36 | −1.9 |
| 7 | 5.19 | −5.1 |

As shown in above Table 11, it was confirmed that the pre-correction value (X) became smaller in accordance with the increase of the concentration of acetaldehyde in the sample. Further, the value of the relative error, which expresses the proportion of the increase/decrease with respect to pre-correction value (X) of Sample 5 (i.e., the proportion, with respect to the pre-correction value (X) of Sample 5, of the value obtained by subtracting 5.47%, which was the pre-correction value (X) of Sample 5, from the pre-correction value (X) of the sample), also became larger as the concentration of the acetaldehyde increased. This showed that the stable A1C amount decreased by being subjected to aldehydation by acetaldehyde.

[Correction in Accordance with Fraction γ]

Next, correction of the pre-correction value (X) of above Table 11 was carried out as shown in following Table 12 by using fraction γ that was adjacent, at a side at which the positive charge amount was smaller, i.e., the side at which the migration speed was faster, to fraction β identified as stable A1c.

TABLE 12

| sample | fraction γ (%) | modification rate (P) (%) | remaining rate (Q) (%) | post-correction value (Y) (%) | relative error (%) |
| --- | --- | --- | --- | --- | --- |
| 5 | 2.4 | — | 100 | 5.47 | 0.0 |
| 6 | 4.6 | 1.6 | 98.4 | 5.45 | −0.3 |
| 7 | 7.3 | 4.3 | 95.7 | 5.42 | −0.8 |

First, the proportion of the area of fraction γ, with respect to the entire peak area of the fractions including hemoglobin, was as shown in the left end column in above Table 12. Specifically, these proportions were 2.4% in Sample 5, 4.6% in Sample 6, and 7.3% in Sample 7.

For the same reason as in above-described Example 1, 3% was deducted from the proportion of the peak area of fraction γ, and this was the value listed as the modification rate (P) shown in above Table 12. Here, fraction γ in Sample 5 was 2.4% and was less than this 3%, and this case was treated as the modification rate (P) being 0 in terms of computation. This showed that the modification rate (P) increased as the concentration of acetaldehyde within the sample increased. Further, for the same reason as in above-described Example 1, appropriate correction is possible even if the proportion of the peak area including aldehydated HbA0, with respect to the entire peak area of the fractions including hemoglobin, is used as the modification rate (P).

The value obtained by subtracting the modification rate (P) from 1 was the remaining rate (Q, expressed as a percentage) in the above table. It was thought that the stable A1c, which remained in the proportion was the pre-correction value (X) of above Table 11, i.e., appeared in the electropherogram as fraction β. Accordingly, the post-correction value (Y) in above Table 12, which was the value obtained by dividing the pre-correction value (X) by the remaining rate (Q), was thought to be the proportion of the total value of the peak area of the fraction including the stable A1c that remained without having been chemically modified, and the peak area of the fraction including the chemically-modified stable A1c, with respect to the entire peak area of the fractions including hemoglobin. Here, from above Table 11, when the absolute value of the relative error based on the pre-correction value (X) was a maximum of 5.1% in Sample 7, from above Table 12, the absolute value of the relative error based on the post-correction value (Y) (i.e., the proportion, with respect to the pre-correction value (X) of Sample 5, of the value obtained by subtracting the pre-correction value (X) of Sample 5 (see FIG. 11), which was thought to not have been affected by chemical modification, from the post-correction value (Y) of the sample) was a maximum of 0.8% in Sample 7. Therefore, by carrying out correction, the range of relative errors that arose due to chemical modification was narrowed.

Accordingly, it can be thought that, due to correction that uses fraction γ, effects of chemical modification due to aldehydation are reduced or eliminated, and a value nearer to the proportion of stable A1c that reflects the average blood sugar level of previous one to two months is determined.

[Correction in Accordance with Fraction δ]

A case is described in which the pre-correction value (X) of above Table 11 was corrected by using fraction δ that was adjacent, at a side at which the positive charge amount was smaller, i.e., the side at which the migration speed was faster, to fraction α identified as HbA0. Note that, in the correction in accordance with fraction δ, as shown in following Table 13, for the same reasons as in above-described Example 1, 4% was deducted, as a predetermined peak area value, from the proportion of the peak area of fraction δ. Further, the peak area of a substance also generated at the time when HbA0 was chemically modified was about 1.65 times the peak area of the aldehydated HbA0 included in fraction γ. From this, by dividing the value, which was obtained by deducting 4% from fraction δ, by the predetermined factor that was this 1.65, the modification rate (P) was derived. In addition, the derivations of the remaining rates (Q), the post-correction values (Y) and the relative errors were the same as in Table 12. However, the post-correction values (Y) in Table 13 were values obtained by dividing the pre-correction values (X) in above Table 11 by the remaining rates (Q) of Table 13. Further, in the same way as in Table 12, the relative error in Table 13 was the proportion, with respect to the pre-correction value (X) of Sample 5, of the value obtained by subtracting the pre-correction value (X) of Sample 5 (see Table 11) that was thought to not have been affected by chemical modification, from the post-correction value (Y) of the sample.

TABLE 13

| sample | fraction δ (%) | fraction δ-4 (%) | modification rate (P) (%) | remaining rate (Q) (%) | post-correction value (Y) (%) | relative error (%) |
|---|---|---|---|---|---|---|
| 5 | 4.5 | 0.5 | 0.3 | 99.7 | 5.49 | 0.3 |
| 6 | 8.1 | 4.1 | 2.5 | 97.5 | 5.50 | 0.6 |
| 7 | 12.6 | 8.6 | 5.2 | 94.8 | 5.48 | 0.1 |

From above Table 13 as well, it can be said that the range of the relative errors of the post-correction value (Y) was smaller than the range of the relative errors of the pre-correction value (X) before correction. Accordingly, it can be thought that, due to correction that uses fraction δ, effects of chemical modification due to aldehydation are reduced or eliminated, and a value nearer to the proportion of stable A1c that reflects the average blood sugar level of previous one to two months is determined.

In a case of carrying out correction by using fraction δ, 1.65 was used as the predetermined factor for dividing the value, which was obtained by deducting 4% from fraction δ (%), in the correction of the effects of carbamylation shown in Example 1. Further, this 1.65 that is the predetermined factor is used similarly in the correction of the effects of aldehydation shown in Example 2. By using the same factor in this way, even in a case in which a substance, which is generated at the time when HbA0 is carbamylated, and a substance, which is generated at the time when HbA0 is aldehydated, are included in the same fraction δ, effects of both of these chemical modifications can be avoided. Note that, in a case in which it is known that the hemoglobin of a sample to be separated and analyzed is not carbamylated, and it is known that the sample is aldehydated, a factor suited to avoiding the effects of aldehydation may be used. The same goes for a case in which it is known that the hemoglobin within a sample to be separated and analyzed is carbamylated and is not aldehydated.

[Summary of Effects of Aldehydation]

As a summary of above Table 11 to Table 13, the relative errors in a case in which correction was not carried out, in a case in which correction was carried out in accordance with fraction γ, and in a case in which correction was carried out in accordance with fraction δ, with respect to the acetaldehyde concentration of each sample, are shown in following Table 14.

TABLE 14

| | acetaldehyde | relative error (%) | | |
|---|---|---|---|---|
| sample | concentration (mg/dL) | no correction | correction using fraction γ | correction using fraction δ |
| 5 | 0 | 0.0 | 0.0 | 0.3 |
| 6 | 12.5 | −1.9 | −0.3 | 0.6 |
| 7 | 25.0 | −5.1 | −0.8 | 0.1 |

Figure 23:
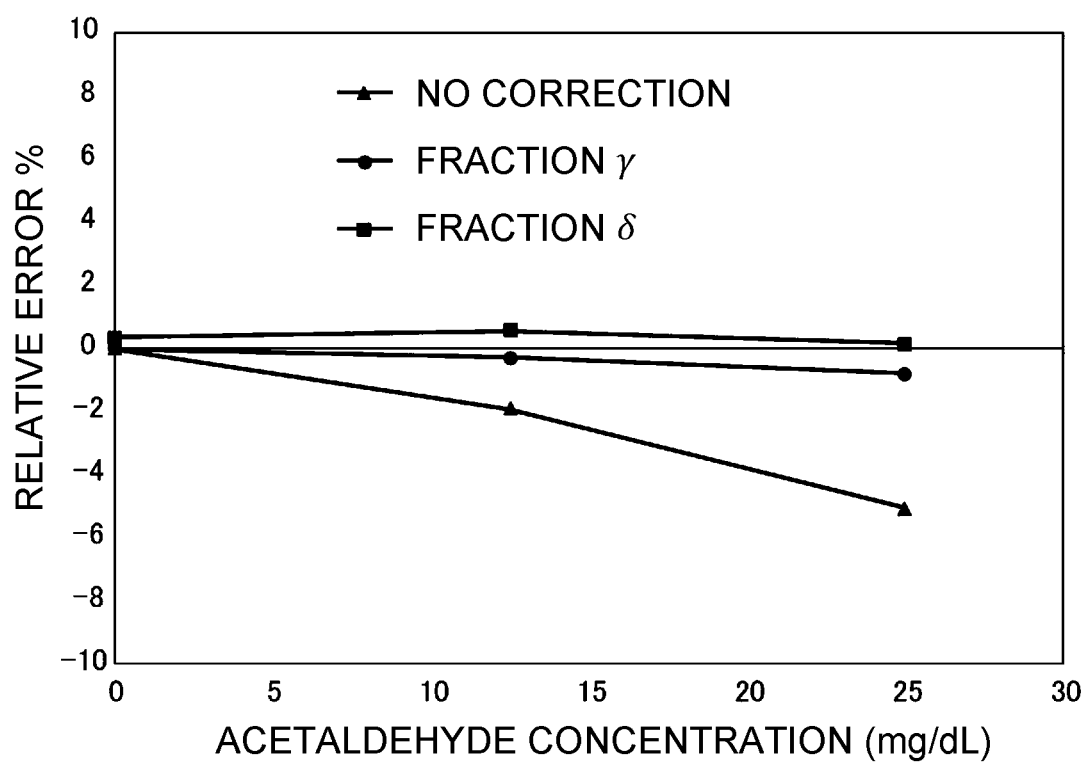
FIG. 23 is a graph showing results of correcting the stable A1c amount in Example 2.

As clearly shown also by FIG. 23 in which the results of above Table 14 are graphed, it is confirmed that effects of aldehydation on stable A1c due to acetaldehyde were at least reduced by both methods of correction.

[First Proportion and Second Proportion]

Note that a case in which it is distinguished whether or not the above-described correction in accordance with fraction γ or fraction δ is to be carried out by using the first proportion and the second proportion, for the pre-correction values (X) shown in above Table 11, is described hereinafter.

The second proportion derived from fraction γ that was adjacent, at a side at which the positive charge amount was smaller, i.e., the side at which the migration speed was faster, to fraction β identified as stable A1c, with respect to the entire peak area of the fractions including hemoglobin, and the first proportion, which was derived from fraction δ that was adjacent, at a side at which the positive charge amount was smaller, i.e., the migration speed was faster, to fraction α identified as HbA0, with respect to the entire peak area including hemoglobin, were as shown in following Table 15.

TABLE 15

| sample | first proportion (fraction δ) (%) | second proportion (fraction γ) (%) |
|---|---|---|
| 5 | 4.5 | 2.4 |
| 6 | 8.1 | 4.6 |
| 7 | 12.6 | 7.3 |

Namely, the second proportions, each of which was the proportion of the area of fraction γ with respect to the entire peak area of the fractions including hemoglobin, were 2.4% in Sample 5, 4.6% in Sample 6, and 7.3% in Sample 7. Further, the first proportions, each of which was the proportion of the area of fraction δ, was 4.5% in Sample 5, 8.1% in Sample 6, and 12.6% in Sample 7.

[Judgement on Necessity of Correction]

It was judged whether or not the first proportion in above Table 15 was greater than or equal to the first threshold value. In the same way as in above-described Example 1, 9% was used for the first threshold value. Similarly, it was judged whether or not the second proportion was greater than or equal to the second threshold value. Here as well, in the same way as in the above-described Example 1, 5% was used as the second threshold value.

First, for Sample 7, the first proportion was greater than or equal to 9% which was the first threshold value, and the second proportion was greater than or equal to 5% which was the second threshold value. Therefore, it was judged that the proportion of the peak area of the fraction including stable A1c, with respect to the peak area of the fraction including HbA0 or the entire peak area of the electropherogram, was to be corrected by the remaining rate. On the other hand, for Sample 5 and Sample 6, the first proportion was less than 9% that was the first threshold value, and the second proportion was less than 5% that was the second threshold value. Therefore, it was judged that the aforementioned correction was not to be carried out.

[Correction in Accordance with Fraction γ]

Next, correction of the pre-correction value (X) of above Table 11 was carried out as shown in following Table 16 by using fraction γ that was adjacent, at a side at which the positive charge amount was smaller, i.e., the side at which the migration speed was faster, to fraction β identified as stable A1c.

TABLE 16

| sample | fraction γ (%) | modification rate (P) (%) | remaining rate (Q) (%) | post-correction value (Y) (%) | relative error (%) |
|---|---|---|---|---|---|
| 5 | 2.4 | — | — | 5.47 | 0.0 |
| 6 | 4.6 | — | — | 5.36 | −1.9 |
| 7 | 7.3 | 4.3 | 95.7 | 5.42 | −0.8 |

First, the proportion of the area of fraction γ with respect to the entire peak area of the fractions including hemoglobin was as shown in the left end column in above Table 13. Specifically, the proportions were 2.4% in Sample 5, 4.6% in Sample 6, and 7.3% in Sample 7.

First, in Sample 5 and Sample 6, as shown in Table 15, in both cases, the first proportion was less than the first threshold value, and further, the second proportion was less than the second threshold value. Accordingly, the pre-correction value (X) was used as the measured value of the stable A1c fraction, without being corrected by the remaining rate (Q). Note that, although the pre-correction values (X) were not corrected in Sample 5 and Sample 6 in this way, for convenience of comparison with the post-correction value (Y) and the relative error of Sample 7, 5.47% and 5.36% that are the pre-correction values (X) were shown in the post-correction value (Y) column in Table 13.

On the other hand, as shown in Table 15, in Sample 7, the first proportion was greater than or equal to the first threshold value, and the second proportion was greater than or equal to the second threshold value. In the same way as in above-described Example 1, as the peak area of fraction γ usually observed in the sample of a healthy individual that was thought to have a usual amount of labile A1c as well and is not subjected to effects of carbamylation and aldehydation, 3%, which was the average value of the peak area of fraction γ of plural healthy individuals, was used as a predetermined peak area, and was deducted from the peak area of fraction γ. The value was the modification rate (P) in above Table 16. The value obtained by subtracting the value from 1 was the remaining rate (Q, expressed as a percentage) in Table 16, and it was thought that the stable A1c that remained in the proportion was the pre-correction value (X) in above Table 11, i.e., appeared in the electropherogram as the fraction β. Accordingly, it was thought that the post-correction value (Y) in above Table 16, which was the value obtained by dividing the pre-correction value (X) by the remaining rate (Q), was the actual stable A1c amount, and the post-correction value (Y) was used as the measured value of the stable A1c fraction. Here, from above Table 11, when the absolute value of the relative error based on the pre-correction value (X) was a maximum of 5.1% in Sample 7, from above Table 16, the absolute value of the relative error based on the post-correction value (Y) (i.e., the relative error was the proportion, with respect to the pre-correction value (X) of Sample 5, of the value obtained by subtracting the pre-correction value (X) of Sample 5 (see Table 11), which was thought to have not been affected by chemical modification, from the post-correction value (Y) of the sample), decreased to 0.8%. Therefore, by judging the necessity of correction, and carrying out correction when it was judged that correction was needed, the range of relative errors that arose due to chemical modification was small.

Accordingly, it can be thought that, by carrying out judgement as to the necessity of correction, and carrying out correction by using fraction γ in a case in which it is judged that correction is needed, effects of chemical modification due to aldehydation are reduced or eliminated, and a value nearer to the proportion of stable A1c that reflects the average blood sugar level of previous one to two months is determined.

[Correction in Accordance with Fraction δ]

Next, correction of the pre-correction values (X) of above Table 11 was carried out as shown in following Table 17 by using fraction δ that was adjacent, at a side at which the positive charge amount was smaller, i.e., the side at which the migration speed was faster, to fraction α identified as HbA0.

TABLE 17

| sample | fraction δ (%) | fraction δ-4 (%) | modification rate (P) (%) | remaining rate (Q) (%) | post-correction value (Y) (%) | relative error (%) |
|---|---|---|---|---|---|---|
| 5 | 4.5 | — | — | — | 5.47 | 0.0 |
| 6 | 8.1 | — | — | — | 5.36 | −1.9 |
| 7 | 12.6 | 8.6 | 5.2 | 94.8 | 5.48 | 0.1 |

First, the proportion of the area of fraction δ with respect to the entire peak area of the fractions including hemoglobin was as shown in the left end column in above Table 17. Specifically, the proportions were 4.5% in Sample 5, 8.1% in Sample 6, and 12.6% in Sample 7.

Here, as described above, in Sample 5 and Sample 6, as shown in Table 15, in both cases, the first proportion was less than the first threshold value, and further, the second proportion was less than the second threshold value. Accordingly, correction by the remaining rate (Q) was not carried out. Although the pre-correction values (X) of Sample 5 and Sample 6 were not corrected, the pre-correction values (X) of 5.47% and 5.36% were shown in the post-correction value (Y) column in Table 17 for convenience of comparison with the post-correction value (Y) and the relative error of Sample 7.

On the other hand, as shown in Table 15, in Sample 7, the first proportion was greater than or equal to the first threshold value, and the second proportion was greater than or equal to the second threshold value. Thus, first, in the same way as in above-described Example 1, as the peak area of fraction δ usually observed in a sample of a healthy individual that was thought to not have been subjected to effects of carbamylation and aldehydation, 4%, which was the average value of the peak areas of fraction δ of plural healthy individuals, was used as a predetermined peak area, and was deducted from the peak area of fraction δ. Further, in the same way as in above Example 1, by dividing, by 1.65 as the above-described predetermined factor, the value obtained deducting 4% as the predetermined peak area value from fraction δ, the proportion of the peak area of aldehydated HbA0 with respect to the entire peak area of the fractions including hemoglobin was derived, and was used as the modification rate (P). In addition, derivation of the remaining rate (Q), the post-correction value (Y) and the relative error were the same as in Table 16. However, the post-correction value (Y) in Table 17 was a value obtained by correcting the pre-correction value (X) in above Table 11 by the remaining rate (Q) of Table 17. Further, in the same way as in Table 16, the relative error in Table 17 was the proportion, with respect to the pre-correction value (X) of Sample 5, of a value obtained by subtracting the pre-correction value (X) of Sample 5 (see Table 11), that was thought to have not been affected by chemical modification, from the post-correction value (Y) of the sample.

From Table 17 as well, it can be said that the range of the relative errors of the post-correction value (Y) was smaller than the range of the relative errors of the pre-correction value (X) before correction (see Table 11). Accordingly, even if a judgment on the necessity of correction is carried out, and correction is carried out by using fraction δ in a case in which correction is judged to be necessary, it can be thought that effects of chemical modification due to aldehydation are reduced or eliminated, and a value nearer to the proportion of stable A1c that reflects the average blood sugar level of previous one to two months is determined.

[Summary of Effects of Aldehydation]

As a summary of above Table 11, Table 16 and Table 17, the relative errors in a case in which the samples that were processed by the respective acetaldehyde concentrations were measured without being corrected, and in a case in which judgment on the necessity of correction was carried out and the sample was measured by using correction in accordance with fraction γ when correction was judged to be necessary, and in a case in which judgment on the necessity of correction was carried out and the sample was measured by using correction in accordance with fraction δ when correction was judged to be necessary, were as shown in following Table 18.

TABLE 18

| sample | acetaldehyde concentration (mg/dL) | relative error (%) | | |
|---|---|---|---|---|
| | | no correction | correction using fraction γ | correction using fraction δ |
| 5 | 0 | 0.0 | 0.0 | 0.0 |
| 6 | 12.5 | −1.9 | −1.9 | −1.9 |
| 7 | 25.0 | −5.1 | −0.8 | 0.1 |

Figure 24:
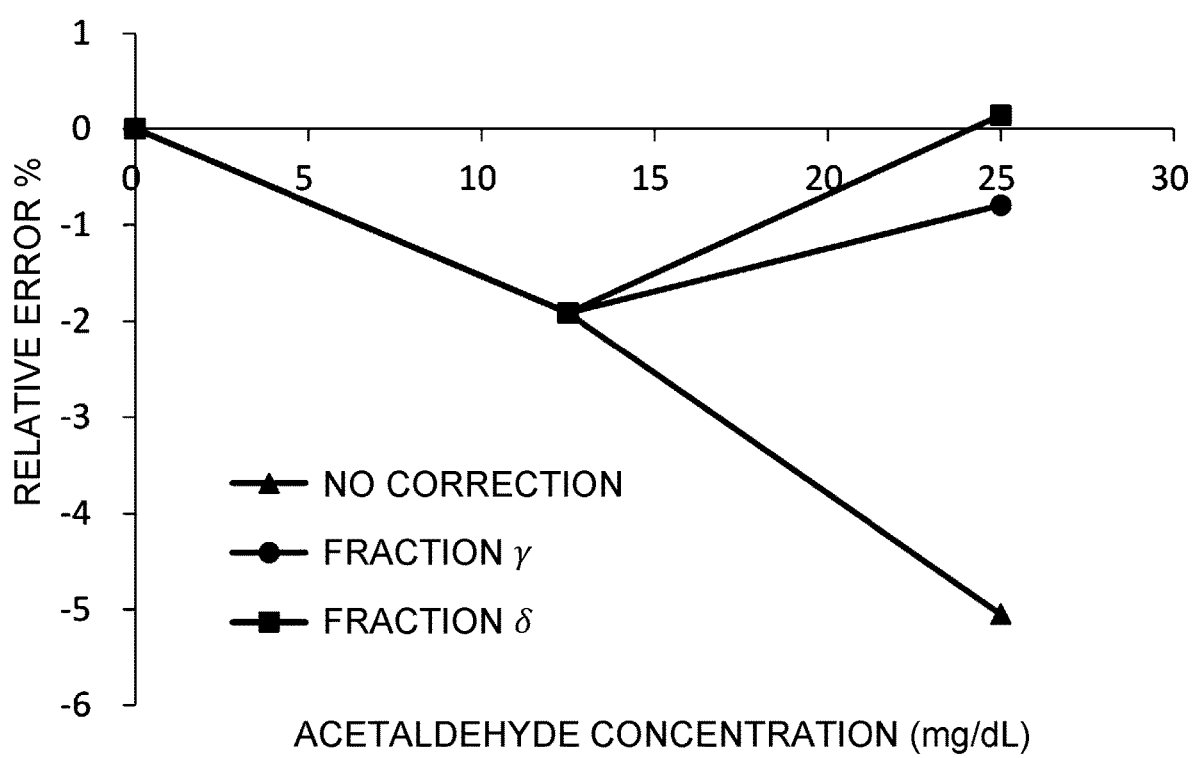
FIG. 24 is a graph showing results of correcting the stable A1c amount in Example 2.

As clearly shown also by FIG. 24 that graphs the relative errors listed in above Table 18 with the acetaldehyde concentration on the horizontal axis, it was confirmed that effects of aldehydation on stable A1c due to acetaldehyde could be reduced by, after carrying out judgment using the first threshold value and the second threshold value, correcting the pre-correction value (X) by the remaining rate (Q) as needed.

Example 3

<Effects of Labile A1c>

The method of measuring stable A1c of the present disclosure was shown to be effective also in samples in which glucose was artificially added to a normal sample and labile A1c was generated.

[Preparation of Sample Containing Labile A1c]

Whole blood collected from a healthy individual was used as the normal sample. D-glucose was added to the normal sample such that the final concentrations shown in following Table 19 were obtained, and Sample 8 to Sample 12 that were incubated at 37° C. were prepared, and each of these was used as the above-described specimen Sa (see FIG. 7). The concentration of labile A1c within the sample increased in accordance with the increase in the concentration of D-glucose within the sample.

TABLE 19

| sample | D-glucose concentration (mg/dL) |
|---|---|
| 8 | 0 |
| 9 | 375 |
| 10 | 750 |
| 11 | 1125 |
| 12 | 1500 |

Note that the concentration of D-glucose within sample 8 of above Table 19 was 0 mg/dL. This means that D-glucose was not added, and the normal sample remained as was. Further, the migration liquid Lm, the dilution liquid Ld, and the mixed specimen Sm were the same as those in above-described Example 1.

[Electropherogram]

Figure 25:
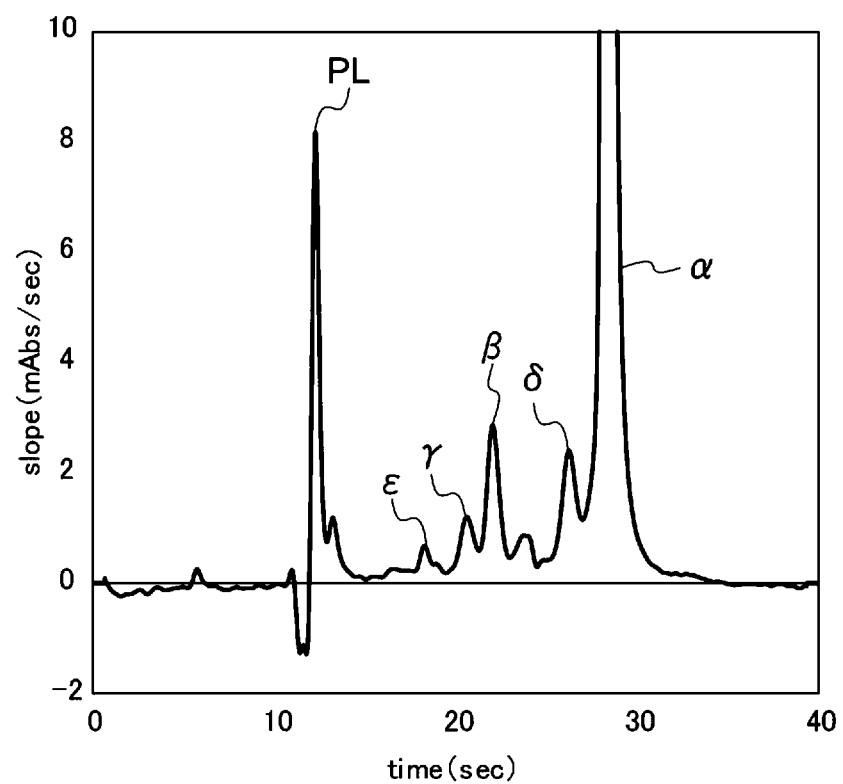
FIG. 25 shows the electropherogram of Sample 8 in Example 3.
Figure 26:
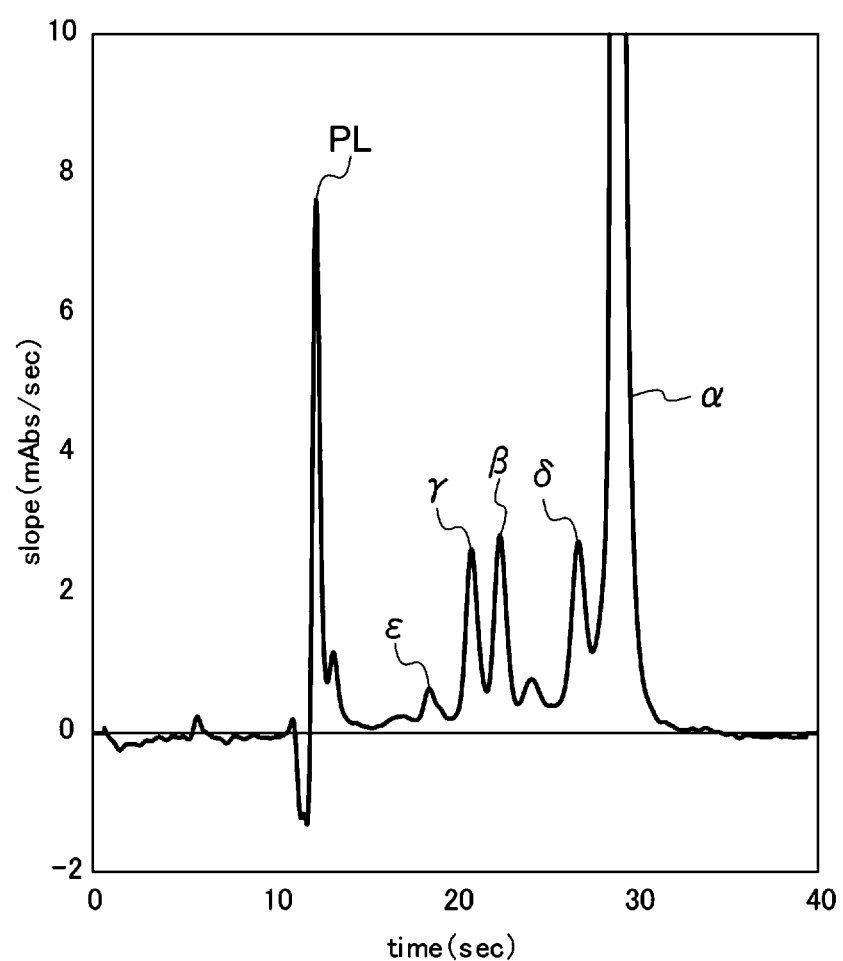
FIG. 26 shows the electropherogram of Sample 9 in Example 3.
Figure 27:
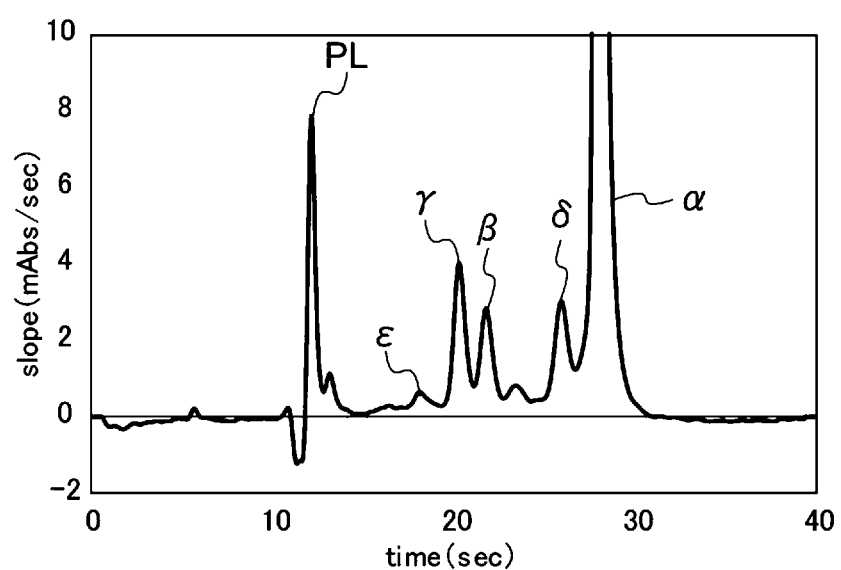
FIG. 27 shows the electropherogram of Sample 10 in Example 3.
Figure 28:
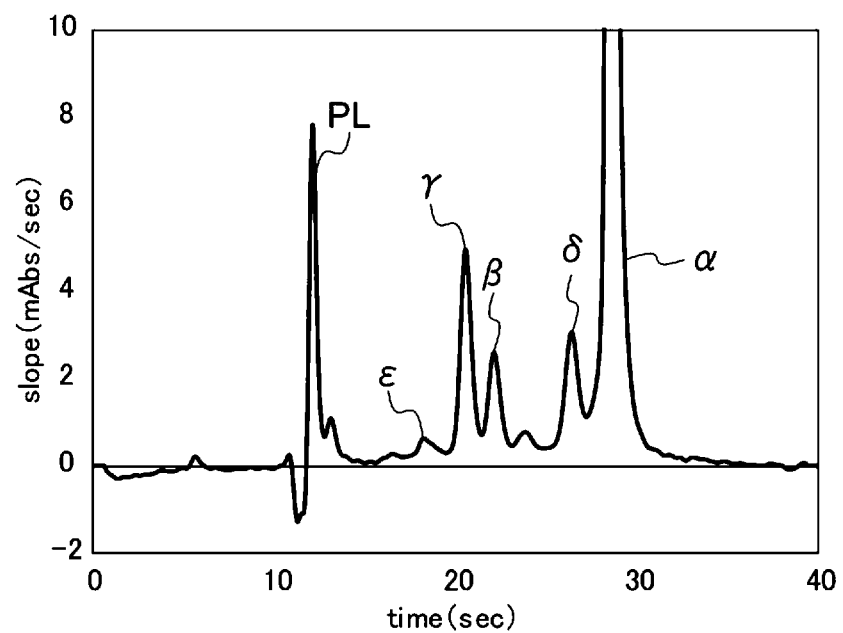
FIG. 28 shows the electropherogram of Sample 11 in Example 3.
Figure 29:
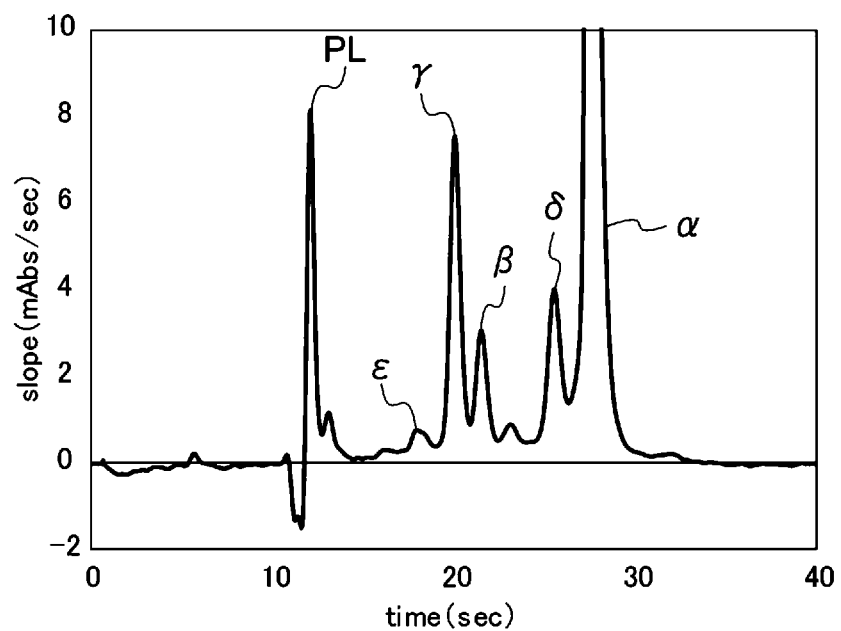
FIG. 29 shows the electropherogram of Sample 12 in Example 3.

An electropherogram was obtained with the point in time at which a voltage was applied being the point in time of the start of the separation analysis, and the point in time at which a voltage was applied being the point in time of 0 seconds. The electropherogram of Sample 8 to which glucose was not added is shown in FIG. 25. The point in time at which the voltage was applied was the point in time of the start of the separation analysis, and was the point in time at which the migration time was 0 seconds in the electropherogram. The interface arrival point in time at which the furthest point PL was detected is in a vicinity of a migration time of 12.3 seconds. Further, fraction E that was the HbF fraction had a peak in the vicinity of a migration time of 18.3 seconds. Fraction β that was the stable A1c fraction had a peak in the vicinity of a migration time of 22.1 seconds. Fraction α that was the HbA0 fraction had a peak in the vicinity of a migration time of 28.4 seconds. Further, fraction γ, which had a peak in the vicinity of a migration time of 20.8 seconds which was earlier than fraction β, was the fraction including labile A1c, but HbA0 subjected to carbamylation and HbA0 subjected to aldehydation were also included in the fraction. Further, a substance that was generated at the time when HbA0 was carbamylated or aldehydated is included in fraction δ that had a peak in the vicinity of a migration time of 26.3 seconds which was earlier than fraction a.

The electropherograms of Sample 9 in which D-glucose was added in a concentration of 375 mg/dL, Sample 10 in which D-glucose was added in a concentration of 750 mg/dL, Sample 11 in which D-glucose was added in a concentration of 1125 mg/dL, and Sample 12 in which D-glucose was added in a concentration of 1500 mg/dL, were as shown in FIG. 26, FIG. 27, FIG. 28 and FIG. 29, respectively. In the same way as in the above-described cases of carbamylation and aldehydation, it was confirmed from FIG. 25 to FIG. 29 that the peak area of fraction γ increased in accordance with an increase of the concentration of D-glucose, which was used in order to create labile A1C, increased It was confirmed that the peak area of fraction δ also increased slightly, but the amount of increase thereof was much smaller than in fraction γ. In this way, even if the amount of labile A1c in the sample was high due to the sample being processed by D-glucose, the peak area of fraction δ did not become large. On the other hand, if the carbamylated HbA0 and/or the aldehydated HbA0 in the sample increased due to the sample being processed by carbamylation and/or aldehydation, the peak area of fraction δ increased. Therefore, by carrying out correction by using the peak area of fraction δ, the effects of carbamylation and aldehydation can be corrected appropriately without being affected by a sample that contains labile A1c.

[Derivation of Pre-Correction Value (X)]

From fraction β in FIG. 25 to FIG. 29, the pre-correction value (X), which was the proportion of the peak area of stable A1c, was derived as in following Table 20. Note that the method of deriving the pre-correction value (X) was the same as in above-described Example 1.

TABLE 20

| sample | pre-correction value (X) (%) | relative error (%) |
| --- | --- | --- |
| 8 | 5.61 | 0.0 |
| 9 | 5.64 | 0.5 |
| 10 | 5.70 | 1.6 |
| 11 | 5.76 | 2.7 |
| 12 | 5.71 | 1.8 |

As shown in above Table 20, it was confirmed that, as the concentration of glucose in the sample became higher, the pre-correction value (X) became slightly higher and did not decrease. Further, the value of the relative error, which expressed the proportion of the increase/decrease with respect to pre-correction value (X) of Sample 8, also hardly changed at all with an increase in the glucose concentration. This showed that the stable A1C amount was hardly affected at all by chemical modification by glucose.

[Correction in Accordance with Fraction γ]

Next, correction of the pre-correction values (X) was carried out as shown in following Table 21 by using fraction γ that was adjacent, at a side at which the positive charge amount was smaller, i.e., the side at which the migration speed was faster, to fraction β identified as stable A1c.

TABLE 21

| sample | fraction γ (%) | modification rate (P) (%) | remaining rate (Q) (%) | post-correction value (Y) (%) | relative error (%) |
| --- | --- | --- | --- | --- | --- |
| 8 | 1.84 | — | 100.0 | 5.61 | 0.0 |
| 9 | 3.53 | 0.5 | 99.5 | 5.67 | 1.1 |
| 10 | 5.08 | 2.1 | 97.9 | 5.82 | 3.8 |
| 11 | 6.76 | 3.8 | 96.2 | 5.99 | 6.7 |
| 12 | 8.53 | 5.5 | 94.5 | 6.04 | 7.7 |

The proportion of the area of fraction γ with respect to the entire peak area of the fractions including hemoglobin was as shown in the left end column in above Table 21. Specifically, the proportions were 1.84% in Sample 8, 3.53% in Sample 9, 5.08% in Sample 10, 6.76% in Sample 11, and 8.53% in Sample 12.

For the same reasons as in above-described Example 1, as the peak area of fraction γ usually observed in the sample of a healthy individual, that was thought to have a usual amount of labile A1c and was not subjected to effects of carbamylation and aldehydation, 3%, which was the average value of the peak areas of fraction γ of plural healthy individuals, was, as a predetermined peak area, deducted from the proportion of the peak area of fraction γ, and this was the numerical value listed as modification rate (P) shown in above Table 21. Here, although fraction γ in Sample 8 is 1.8 which was less than this 3%, in terms of computation, this case could be treated as the modification rate (P) being 0.

The value obtained by subtracting the modification rate (P) from 1 was the remaining rate (Q, expressed as a percentage) in above Table 21. Then, the pre-correction value (X) was divided by the remaining rate (Q), and the post-correction value (Y) in above Table 21 was derived. Then, the relative error in a case of carrying out correction by using fraction γ was derived from the post-correction value (Y). Namely, the proportion, with respect to the pre-correction value (X) of Sample 8, of the value obtained by subtracting the pre-correction value (X) of Sample 8 (see Table 20) from the post-correction value (Y) of the sample, was the relative error in above Table 21.

[Correction in Accordance with Fraction δ]

Next is described a case of carrying out correction of the pre-correction values (X) of above Table 20 by using fraction δ that was adjacent, at a side at which the positive charge amount was smaller, i.e., the side at which the migration speed was faster, to fraction α identified as HbA0, as shown in following Table 22. Note that, in the correction in accordance with fraction δ, for the same reasons as in above-described Example 1, 4% was deducted as the predetermined peak area value from the proportion of the peak area of fraction δ. The peak area of a substance, which was also generated at the time when HbA0 was chemically modified, was about 1.65 times the peak area of the aldehydated HbA0 included in fraction δ. From this, the modification rate (P) was derived by dividing, by 1.65 as a predetermined factor, the value obtained deducting 4% from fraction δ. In addition, the derivation of the remaining rate (Q), the post-correction value (Y) and the relative error were the same as in Table 21. However, the post-correction value (Y) in Table 22 was a value obtained by dividing the pre-correction value (X) in above Table 20 by the remaining rate (Q) of Table 22. Further, in the same way as in Table 21, the relative error in Table 22 was the proportion, with respect to the pre-correction value (X) of Sample 8, of the value obtained by subtracting the pre-correction value (X) of Sample 8 (see Table 20) from the post-correction value (Y) of the sample.

TABLE 22

| sample | fraction δ (%) | fraction δ-4 (%) | modification rate (P) (%) | remaining rate (Q) (%) | post-correction value (Y) (%) | relative error (%) |
|---|---|---|---|---|---|---|
| 8 | 3.79 | — | 0.0 | 100.0 | 5.61 | 0.0 |
| 9 | 4.52 | 0.52 | 0.3 | 99.7 | 5.66 | 0.9 |
| 10 | 4.69 | 0.69 | 0.4 | 99.6 | 5.72 | 2.0 |
| 11 | 5.30 | 1.30 | 0.8 | 99.2 | 5.81 | 3.5 |
| 12 | 5.87 | 1.87 | 1.1 | 98.9 | 5.78 | 2.9 |

[Summary of Effects of Labile A1c]

As a summary of above Table 20 to Table 22, the relative errors in a case in which the samples that were processed by the respective glucose concentrations were corrected in accordance with fraction γ, and in a case in which the samples were corrected in accordance with fraction δ, are listed in following Table 23.

TABLE 23

| sample | D-glucose concentration (mg/dL) | relative error (%) correction using fraction γ | relative error (%) correction using fraction δ |
|---|---|---|---|
| 8 | 0 | 0.0 | 0.0 |
| 9 | 375 | 1.1 | 0.9 |
| 10 | 750 | 3.8 | 2.0 |
| 11 | 1125 | 6.7 | 3.5 |
| 12 | 1500 | 7.7 | 2.9 |

Figure 30:
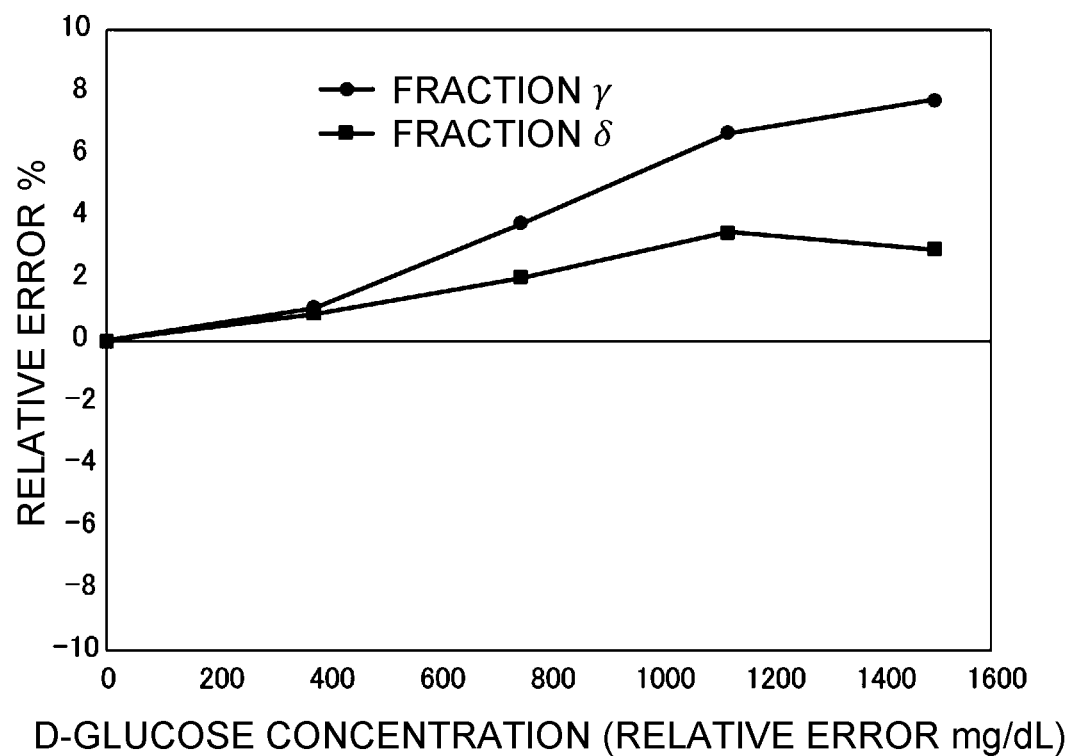
FIG. 30 is a graph showing results of correcting the stable A1c amount in Example 3.

As clearly shown also by FIG. 30 that graphs above Table 23, the relative errors were smaller in the correction using fraction δ than in the correction using fraction γ. This was because, although the peak area of fraction γ was affected by labile A1c, the peak area of fraction δ was not affected by the labile A1c amount. Namely, by carrying out correction by using the fraction including a substance generated together with chemically-modified HbA0 at the time when the HbA0 was chemically-modified, the stable A1c could be correctly measured even if the sample contains labile A1c. Accordingly, it is confirmed that the method of measuring stable A1c that carries out the above-described correction is more effective than correction using a fraction including chemically-modified HbA0.

Note that, as in the following description, if correction is carried out in a case in which the peak area of fraction δ exceeds a given value, erroneous correction of a sample whose content of carbamylated HbA0 and/or aldehydated HbA0 is small and whose content of labile A1c is large can be avoided.

[First Proportion and Second Proportion]

The first proportion and the second proportion were derived in the same way as in Example 1 and Example 2. The results thereof were as shown in following Table 24.

TABLE 24

| sample | first proportion (fraction δ) (%) | second proportion (fraction γ) (%) |
|---|---|---|
| 8 | 3.8 | 1.8 |
| 9 | 4.5 | 3.5 |
| 10 | 4.7 | 5.1 |
| 11 | 5.3 | 6.8 |
| 12 | 5.9 | 8.5 |

Namely, the second proportions each of which was the proportion of the area of fraction γ were 1.8% in Sample 8, 3.5% in Sample 9, 5.1% in Sample 10, 6.8% in Sample 11, and 8.5% in Sample 12. Further, the first proportions each of which was the proportion of the area of fraction δ were 3.8% in Sample 8, 4.5% in Sample 9, 4.7% in Sample 10, 5.3% in Sample 11 and 5.9% in Sample 12.

[Judgment by First Threshold]

It was judged whether or not the first proportions in above Table 24 were greater than or equal to the first threshold value. In the same way as in Example 1 and Example 2, 9% was used as the first threshold value.

In each of Sample 8 to Sample 12, the first proportion was less than 9% that was the first threshold value. Therefore, it was judged that correction by the remaining rate was not to be carried out with respect to the proportion of the peak area of the fraction including stable A1c, with respect to either the peak area of the fraction including HbA0 or the entire peak area of the electropherogram, in Sample 8 through Sample 12.

Namely, judgement was carried out on the necessity of correction, and the correction errors of the stable A1c fraction in accordance with the measuring method of the present invention in a case in which it was judged that correction was not needed, were as shown in above Table 20.

[When Judgement is not Carried Out]

Here, explanation is given of a case in which Sample 8 to Sample 12 were corrected in accordance with the remaining rate and were measured, without carrying out the above-described judgment in accordance with the first threshold value. In this case, there is no step of distinguishing whether or not the first proportion is greater than or equal to the first threshold value. Therefore, for each of Sample 8 to Sample 12, the proportion of the peak area of the fraction including stable A1c, with respect to either the peak area of the fraction including HbA0 or the entire peak area of the electropherogram, was corrected by using the remaining rate. The results of measurement in the case of carrying out correction by using fraction γ were as shown in following Table 25.

TABLE 25

| sample | fraction γ (%) | modification rate (P) (%) | remaining rate (Q) (%) | post-correction value (Y) (%) | relative error (%) |
|---|---|---|---|---|---|
| 8 | 1.8 | — | — | 5.61 | 0.0 |
| 9 | 3.5 | 0.5 | 99.5 | 5.67 | 1.1 |
| 10 | 5.1 | 2.1 | 97.9 | 5.82 | 3.8 |
| 11 | 6.8 | 3.8 | 96.2 | 5.99 | 6.7 |
| 12 | 8.5 | 5.5 | 94.5 | 6.04 | 7.7 |

The proportion of the area of fraction γ with respect to the entire peak area of the fractions including hemoglobin was as shown in the left end column in above Table 25. Specifically, these proportions were 1.8% in Sample 8, 3.5% in Sample 9, 5.1% in Sample 10, 6.8% in Sample 11, and 8.5% in Sample 12.

For the same reasons as in above-described Example 1, as the peak area of fraction γ usually observed in a sample of a healthy individual that was thought to have a normal labile A1c amount and that was not subjected to effects of carbamylation and aldehydation, 3%, which was the average value of the peak areas of fraction γ of plural healthy individuals, was deducted, as the predetermined peak area, from the peak area of fraction γ. This was the value listed as the modification rate (P) shown in above Table 25. Here, fraction γ in Sample 8 was 1.8% which was below this 3%, and this case was treated as the modification rate (P) being 0 in terms of computation.

The value obtained by subtracting the modification rate (P) from 1 was the remaining rate (Q, expressed as a percentage) in above Table 25. Further, the pre-correction value (X) was divided by the remaining rate (Q), and the post-correction value (Y) in above Table 25 was derived. Further, the relative error in a case in which correction was carried out by using fraction γ was derived from the post-correction value (Y). Namely, the proportion, with respect to the pre-correction value (X) of Sample 8, of the value obtained by subtracting the pre-correction value (X) of Sample 8 (see Table 24) from the post-correction value (Y) of the sample, was the relative error in above Table 25.

[Summary of Effects of Labile A1c]

As a summary of the above, the relative errors in a case in which the samples which were processed by the respective glucose concentrations were subjected to correction without the distinguishing step being carried out, and a case in which correction was not carried out on the basis of the results of a distinguishing step, are listed in following Table 26.

TABLE 26

| sample | D-glucose concentration (mg/dL) | relative error (%) without judgement step | relative error (%) with judgement step |
| --- | --- | --- | --- |
| 8 | 0 | 0.0 | 0.0 |
| 9 | 375 | 1.1 | 0.5 |
| 10 | 750 | 3.8 | 1.6 |
| 11 | 1125 | 6.7 | 2.7 |
| 12 | 1500 | 7.7 | 1.8 |

Figure 31:
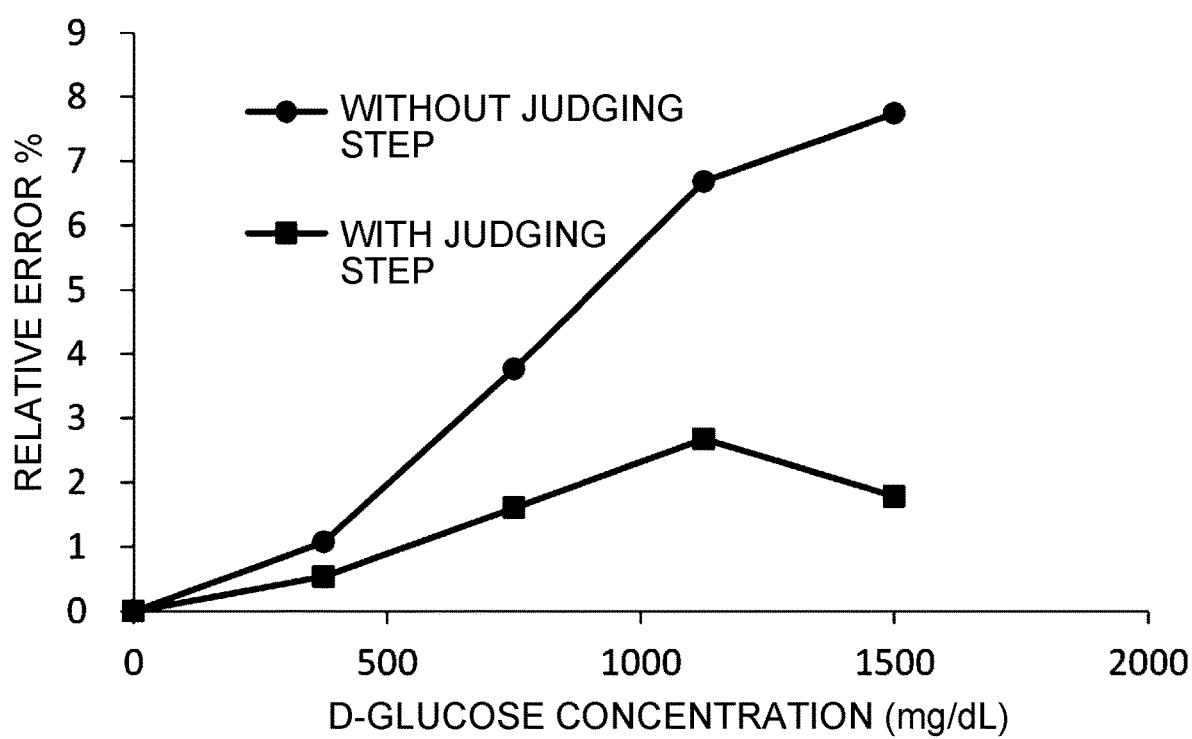
FIG. 31 is a graph showing the results of a distinguishing step in Example 3.

As clearly shown also by FIG. 31 that graphs the relative errors listed in above Table 26 with the D-glucose concentration on the horizontal axis, in a case in which correction was carried out without the distinguishing step having been carried out, the relative errors were greater than in a case in which correction was not carried out on the basis of results of having carried out the distinguishing step. This was because the remaining rate was derived and the correction was carried out by using the peak area of the labile A1c included in fraction γ as the peak area of the carbamylated HbA0 or the aldehydated HbA0. On the other hand, by carrying out the distinguishing step, worsening of the relative error due to excessive correction was avoided. This was because the necessity of correction with respect to the effects of carbamylation and aldehydation is judged from the value of the peak area of fraction δ that was not affected by labile A1c. Accordingly, it was confirmed that the correction that has the distinguishing step at least reduces the effects of the labile A1c contained in the sample.

INDUSTRIAL APPLICABILITY

The present invention can be used in measuring devices that measure stable hemoglobin A1c among fractions of bloodstream hemoglobin.

What is claimed is:

1. A method of measuring stable A1c in a blood sample based on a time distribution of an optical measured value of hemoglobin at a flow path which separates hemoglobin in the blood sample on a basis of amounts of charges of hemoglobin, the method comprising:
   a step of obtaining a correction factor, based on a proportion (A/(A+G)) of a peak area (A) of a fraction including HbA0 in the time distribution divided by a total value (A+G) of the peak area (A) and a peak area (G) of a first fraction including chemically-modified HbA0 in the time distribution; and
   a step of correcting, based on the correction factor, a peak area of a fraction including stable A1c in the time distribution.

2. The method of measuring stable A1c of claim 1, wherein the correction factor is obtained as a remaining rate representing a proportion of HbA0 that remains in the blood sample without having been chemically modified.

3. The method of measuring stable A1c of claim 1, further comprising:
   a step of distinguishing whether or not a first proportion is greater than or equal to a first threshold value, the first proportion representing a proportion of a peak area (D) of a second fraction including a component having a smaller amount of positive charge than HbA0 adjacent to a fraction identified as HbA0, with respect to either the peak area (A) of the fraction including HbA0, or an entire peak area of the time distribution, the first threshold value having been previously determined from the first proportion obtained by measuring samples of healthy individuals,
   wherein the peak area of the fraction including stable A1c is corrected further based on a determination of whether the first proportion is greater than or equal to the first threshold value.

4. The method of measuring stable A1c of claim 3, further comprising:
   a step of distinguishing whether or not a second proportion is greater than or equal to a second threshold value, the second proportion representing a proportion of the peak area (G) of the first fraction, with respect to either the peak area (A) of the fraction including HbA0 or an entire peak area of the time distribution, the second threshold value having previously been determined from the second proportion obtained by measuring samples of healthy individuals,
   wherein the peak area of the fraction including stable A1c is corrected further based on a determination of whether the first proportion is greater than or equal to the first threshold value, and the second proportion is greater than or equal to the second threshold value.

5. The method of measuring stable A1c of claim 1, wherein the peak area (G) is an estimated value obtained from a peak area (D) of a second fraction including a component having a smaller amount of positive charge than HbA0 adjacent to a fraction identified as HbA0, based on a correlation relationship between the peak area (G) and the peak area (D) having previously been determined by measuring blood samples of healthy individuals.

6. The method of measuring stable A1c of claim 5, wherein to obtain the correction factor, the peak area (G) is represented by a ratio (D/a), where the peak area (D) has previously been divided by a predetermined factor (a) having previously been determined from the correlation relationship between the peak area (D) and the peak area (G), such that the correction factor is determined as A/((D/a)+A).

7. The method of measuring stable A1c of claim 6, wherein the total value (A+G) is approximated by an entire peak area (E) of fractions including hemoglobin in the time distribution, such that the correction factor is determined as $1-((D/a)/E)$.

8. The method of measuring stable A1c of claim 7, wherein the peak area (D) is updated by deducting a predetermined value (b) from the peak area (D), the predetermined value (b) being determined in advance from a peak area (D) of the second fraction by measuring samples of healthy individuals, such that the correction factor is determined as $1-((D-b)/a)/E$.

9. The method of measuring stable A1c of claim 1, wherein the total value (A+G) is approximated by an entire peak area (E) of fractions including hemoglobin in the time distribution, such that the correction factor is determined as $1-(G/E)$.

10. The method of measuring stable A1c of claim 9, wherein the peak area (G) is updated by deducting a predetermined peak area value (c) from the peak area (G), the predetermined peak area value (c) being determined in advance from a peak area (G) of the first fraction by measuring samples of healthy individuals, such that the correction factor is determined as $1-((G-c)/E)$.

11. The method of measuring stable A1c of claim 1, wherein the chemical modification is at least one of carbamylation or aldehydation.

12. The method of measuring stable A1c of claim 1, wherein the time distribution is a chromatogram.

13. The method of measuring stable A1c of claim 1, wherein the time distribution is an electropherogram obtained by capillary electrophoresis.

\* \* \* \* \*